United States Patent [19]

Sendai et al.

[11] Patent Number: 5,438,053
[45] Date of Patent: Aug. 1, 1995

[54] CEPHEM COMPOUNDS COMPOSITIONS AND METHOD

[75] Inventors: Michiyuki Sendai, Suita; Kenji Okonogi, Shimamoto, both of Japan

[73] Assignee: Takeda Chemical Industries, Ltd., Osaka, Japan

[21] Appl. No.: 92,080

[22] Filed: Jul. 16, 1993

[30] Foreign Application Priority Data

Jul. 17, 1992 [JP] Japan .................. 4-191158
Feb. 10, 1993 [JP] Japan .................. 5-022896

[51] Int. Cl.⁶ .................. C07D 501/36; A61K 31/545
[52] U.S. Cl. .................. 514/206; 540/227
[58] Field of Search .................. 540/227; 514/206, 202

[56] References Cited

U.S. PATENT DOCUMENTS 5,057,511  10/1991  Jung et al. .................. 514/206
5,124,037  5/1993   Kubota et al. .................. 540/227

FOREIGN PATENT DOCUMENTS 0241901  10/1987  European Pat. Off. .
0544166  6/1993   European Pat. Off. .
4221388  8/1992   Japan .
4270290  9/1992   Japan .

Primary Examiner—Nicholas Rizzo
Attorney, Agent, or Firm—Foley & Lardner

[57] ABSTRACT

Novel cephem compounds having, at the 3-position of the cephem nucleus, a group of the formula:

$$-CH_2-S-A-Y-B$$

wherein A stands for a further optionally substituted divalent nonionic aromatic heterocyclic group bounded to the adjacent sulfur atom via carbon atom, Y stands for a bond, a sulfur atom, an oxygen atom, NH, CONH, $SO_2NH$ or a divalent $C_1$-$C_6$ hydrocarbon chain optionally including one or two selected from the group consisting of sulfur atom, oxygen atom, NH group, CONH group and $SO_2NH$ group in the chain, and B stands for a group of the formula:

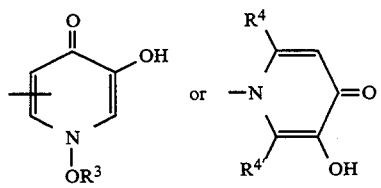

wherein $R^3$ stands for H or an optionally substituted lower alkyl, $R^4$ and $R^{4'}$ each stand for H, OH, an optionally substituted lower alkyl, COOH or CONH, or salts thereof, having excellent antibacterial activities especially against *Pseudomonas aeruginosa* and keeping effective serum levels over a long period.

6 Claims, No Drawings

CEPHEM COMPOUNDS COMPOSITIONS AND METHOD

This invention relates to novel cephem compounds or their salts possessing excellent antimicrobial activities. The cephem compounds or their salts of this invention are used as antimicrobial agents.

Jung et al., U.S. Pat. No. 5,057,511 and EP-A-241901 disclose cephem compounds having on the heterocyclic ring of a hetrocyclic ring thiomethyl group at the 3-position of the cephem nucleus a substituent of the formula:

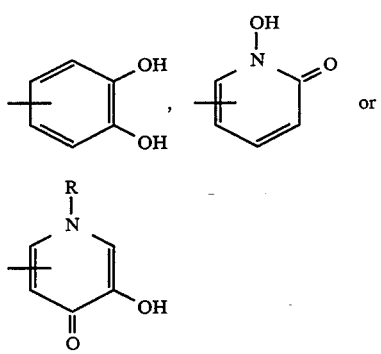

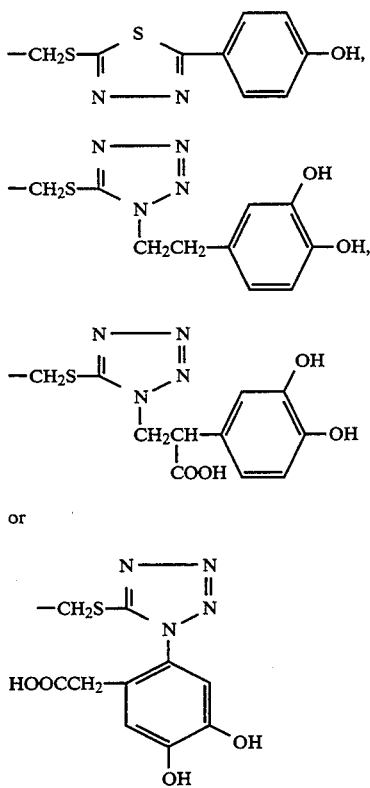

wherein R stands for hydrogen or $C_{1-4}$ alkyl, which compounds possess good antibacterial activity against *Pseudomonas aeruginosa*.

In Jung et al., U.S. Pat. No. 5,057,511, there is specific disclosure focused upon a cephem compound having as a 3-substituent of the cephem nucleus a group of the formula:

There is no disclosure of any synthesis of any compound having in the 3-substituent the group of the formula:

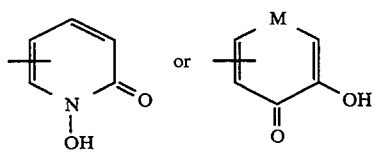

wherein M stands for oxygen atom or a group $NR^3$ wherein $R^3$ stands for hydrogen atom or $C_{1-4}$ alkyl group.

And, in EP-A-241901, a cephem compound having on the heterocyclic thiomethyl group at the 3-position of the cephem nucleus a substituent of the formula:

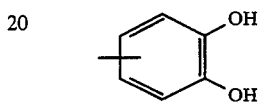

is disclosed and a practical embodiment of its synthesis is given, but there is no disclosure of such a cephem compound as having a substituent of the formula:

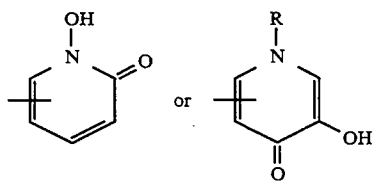

Further, in JPA S63(1988)-188685, cephem compounds are disclosed having as a 3-substituent of the cephem nucleus a group of the formula:

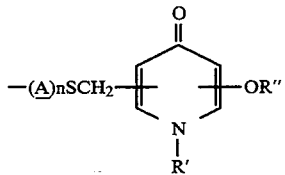

wherein A stands for a lower alkylene or a lower alkenylene; n denotes 0 or 1; R' stands for hydrogen or a lower alkyl group; and R" stands for hydrogen or a hydroxyl- protecting group, but these compounds have no heterocyclic ring between S and the group of the formula:

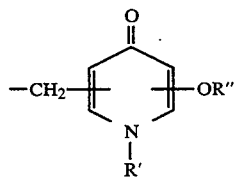

Presently, a variety of cephem compounds have been launched into markets, but antimicrobial activities of them are not fully satisfactory, and there is still the need for creating compounds having potent antimicrobial activities against a broad spectrum of both Gram-positive and Gram-negative bacteria. Especially desired are creation of compounds having potent antibacterial activities against *Pseudomonas aeruginosa*, causative organisms of refractory infections, and maintaining effective serum levels over a long period.

The present invention contemplates cephem compounds having a hydroxypyridonyl group as the substituent on the heterocyclic ring of the heterocyclic thiomethyl group at the 3-position of its cephem nucleus, which have never been actually synthesized and their medicinal effects have never been searched. As a result, they succeeded in synthesizing, for the first time, a cephem compound having, as the substituent, a group of the formula:

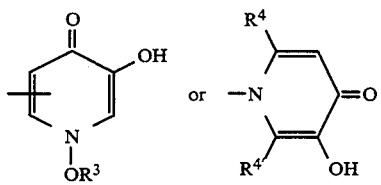

wherein $R^3$ stands for a hydrogen atom or an optionally substituted lower alkyl group; $R^4$ and $R^{4'}$ respectively stand for a hydrogen atom, a hydroxyl group, an optionally substituted lower alkyl group, a carboxyl group or a carbamoyl group, and further found that the compound possesses an unexpectedly potent antimicrobial activities and keeps effective serum levels over a long period. Based on these findings, the present invention was accomplished.

More specifically, the present invention relates to
(1) a cephem compound having, at the 3-position of the cephem nucleus, a substituent of the formula (II):

$$-CH_2-S-A-Y-B \qquad (II)$$

wherein A stands for an optionally further substituted divalent nonionic aromatic heterocyclic group bonded to the adjacent sulfur atom via carbon atom; Y stands for a bond, a sulfur atom, an oxygen atom, NH, CONH, SO$_2$NH or a divalent C$_1$-C$_5$ hydrocarbon chain optionally including one or two selected from the group consisting of sulfur atom, oxygen atom, NH group, CONH group and SO$_2$NH group in the chain; and B stands for a group of the formula:

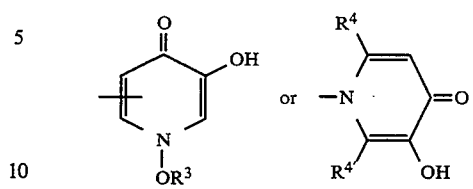

wherein $R^3$ stands for hydrogen atom or an optionally substituted lower alkyl group; and $R^4$ and $R^{4'}$ each stand for hydrogen atom, a hydroxyl group, an optionally substituted lower alkyl group, a carboxyl group or a carbamoyl group (hereinafter simply referred to as "Compound (I)"), or a salt thereof, (1') a cephem compound having, at the 3-position of the cephem nucleus, a substituent of the formula (II'):

$$-CH_2-S-A'-Y-B' \qquad (II')$$

wherein A' stands for an optionally further substituted divalent aromatic heterocyclic group bonded to the adjacent sulfur atom via carbon atom; Y is as defined above; and B' stands for a group of the formula:

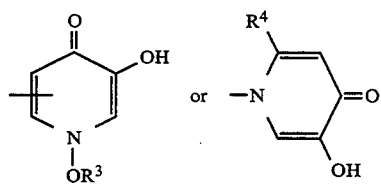

wherein $R^3$ and $R^4$ are as defined above (hereinafter simply referred to as "Compound (I')"), or a salt thereof, (2) a cephem compound of the formula (III):

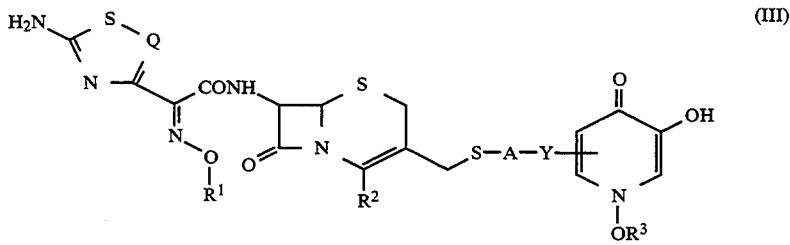

wherein Q stands for N, CH, CCl or CF; $R^1$ stands for hydrogen atom or an optionally substituted hydrocarbon group; $R^2$ stands for an optionally esterified carboxyl group; A, Y and $R^3$ are as defined above, or a salt thereof, (3) a cephem compound of the formula (IV):

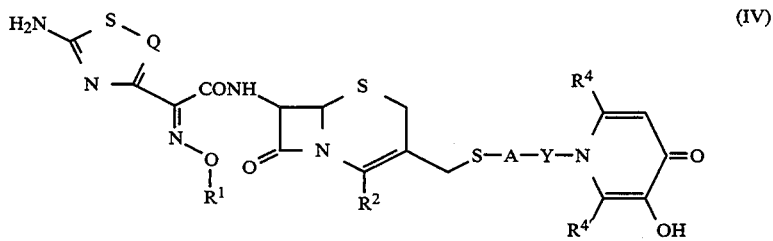

wherein each symbol is as defined above, or a salt thereof, (4) a process for producing the Compound (I) or a salt thereof, which comprises reacting a cephem compound having, at the 3-position of the cephem nucleus, a substituent of the formula (VIII):

$$-CH_2-R^{20} \qquad (VIII)$$

wherein $R^{10}$ stands for a hydroxyl group, an acyloxy group or a halogen atom, or a salt thereof with a compound of the formula (X):

$$HS-A-Y-B \qquad (X)$$

wherein each symbol is as defined above, or a salt thereof, and 5) an antimicrobial composition containing the Compound (I) or a pharmaceutically acceptable salt thereof.

The Compound (I) or Compound (I') having, at the 3-position of the cephem nucleus, a substituent represented by the formula (II) or (II'), or a salt thereof of this invention shows excellent antimicrobial activities in a wide range of Gram-positive bacteria as well as Gram-negative bacteria including *Pseudomonas aeruginasa-* while showing excellent serum levels over a long period.

In the above-mentioned formulae, A represents a divalent nonionic aromatic heterocyclic group optionally having, besides —Y—B (wherein symbols are as defined above), further substituents, and bonds to the adjacent sulfur atom (including that shown by Y) via the carbon atom constituting said heterocyclic group. A' represents a divalent aromatic heterocyclic group optionally having, besides —Y—B' (wherein symbols are as defined above), further substituents, and bonds to the adjacent sulfur atom (including that shown by Y) via the carbon atom constituting said heterocyclic group. As the divalent aromatic heterocyclic group for A', a typical one of which is the divalent nonionic aromatic heterocyclic group for A, mention is made of a divalent group formed by eliminating two hydrogen atoms from a 5- or 6-membered heterocyclic ring having 1 to 4 hetero-atoms such as nitrogen atom, oxygen atom and sulfur atom, among others, as exemplified by a divalent group formed by eliminating two hydrogen atoms from thiazole, isothiazole, thiadiazole, triazole, tetrazole, pyridine, pyrimidine, pyridazine, oxazole, isoxazole, imidazole, pyrazole, oxadiazole, thiophene, furan, pyrazine, triazine, etc.

These aromatic heterocyclic groups may be substituted with, for example, a lower alkyl group (e.g. a $C_{1-6}$ alkyl group such as methyl, ethyl, propyl, isopropyl, butyl, etc.), a lower alkenyl group (e.g. a $C_{2-6}$ alkenyl group such as vinyl, butenyl, propenyl, etc.), amino group, a mono- or di-lower alkylamino group (e.g. a mono- or di- $C_{1-6}$ alkylamino group such as methylamino, ethylamino, dimethylamino, etc.), amidino group, an acyl group (e.g. a $C_{1-6}$ alkanoyl group such as formyl, acetyl, propionyl, etc.), carbamoyl group, a mono- or di-lower alkylcarbamoyl group (e.g. a mono- or di- $C_{1-6}$ alkyl-carbamoyl group such as methylcarbamoyl, ethylcarbamoyl, dimethylcarbamoyl, etc.), sulfamoyl, a mono- or di-lower alkylsulfamoyl group (e.g. a mono- or di- $C_{1-6}$ alkylsulfamoyl group such as methylsulfamoyl, ethylsulfamoyl, dimethylsulfamoyl, etc.), carboxyl group, a lower alkoxycarbonyl group (e.g. a $C_{1-6}$ alkoxycarbonyl group such as methoxycarbonyl, ethoxycarbonyl, etc.), hydroxyl group, a lower alkoxy group (e.g. a $C_{1-6}$ alkoxy group such as methoxy, ethoxy, etc.), a lower alkenyloxy group (e.g. a $C_{2-6}$ alkenyloxy group such as allyloxy, 2-butenyloxy, etc.), mercapto group, a lower alkylthio group (e.g. a $C_{1-6}$ alkylthio group such as methylthio, ethylthio, etc.), sulfo group, cyano group, azido group, halogen (e.g. fluorine, chlorine, bromine, etc.), among others. Number of these substituents ranges preferably 1 to 3, and, when the number is plural, those substituents may be the same as or different from one another. And, the substituent may be on either carbon atom or nitrogen atom of the aromatic heterocyclic group. Among these, as A or A', a 5-membered nonionic aromatic heterocyclic group which includes two to four hetero atoms selected from nitrogen atom and sulfur atom and which may be substituted with cyano group or methyl group, is preferable, and more preferably is a group shown by

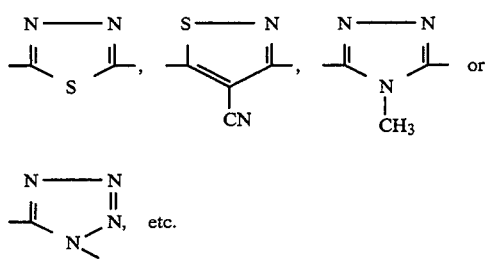

In the above formulae, Y stands for a bond or a sulfur atom, an oxygen atom, NH, CONH, $SO_2NH$ or a divalent $C_1$-$C_6$ hydrocarbon chain optionally including one or two selected from the group consisting of sulfur atom, oxygen atom, NH group, CONH group and $SO_2NH$ group in the chain. The divalent $C_1$-$C_6$ hydrocarbon chain includes a straight-chain or branched $C_1$-$C_6$ alkylene or a $C_{2-6}$ alkenylene group. As the alkylene group, use is made of, for example, methylene, ethylene, trimethylene, tetramethylene, etc., and, as the alkenylene group, use is made of, for example, vinylene, propenylene, butenylene, etc. The optional moieties included in the divalent $C_1$-$C_6$ hydrocarbon chain are arranged that, for example, a sulfur atom, an oxygen atom, NH group, CONH group, or $SO_2NH$ group is present at one or both terminals of the chain or between adjacent carbon atoms in the alkylene or alkenylene chain. The above-mentioned CONH means —CONH— or —NHCO— with this direction, and $SO_2NH$ mean-s—$SO_2NH$— or —$NHSO_2$—, respectively. Among them, preferable examples of Y include groups shown by —S—$(CH_2)_n$—, —$(CH_2)_n$— or —$(CH_2$-$)_n$—CONH— (wherein n denotes a whole number of 0 to 3), etc.

In the above formulae, B stands for a group represented by the formula:

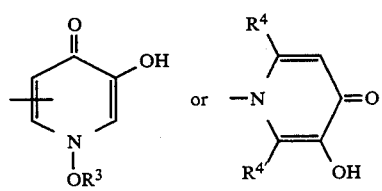

wherein symbols are as defined above. Herein, $R^3$ stands for hydrogen atom or an optionally substituted lower alkyl group (e.g. $C_{1-6}$ alkyl group such as methyl, ethyl, propyl, etc.); $R^4$ and $R^{4'}$ each stand for hydrogen atom, a hydroxyl group, an optionally substituted lower alkyl group (e.g. $C_{1-6}$ alkyl group such as methyl, ethyl, propyl, etc.), a carboxyl group or a carbamoyl group, respectively. In the case where $R^3$, $R^4$ and $R^{4'}$ stand for an optionally substituted lower alkyl group, "substituents" to be employed are exemplified by a lower alkenyl group (e.g. a $C_{2-6}$ alkenyl group such as vinyl, butenyl, propenyl, etc.), amino group, a mono- or di- lower alkylamino group (e.g. a mono- or di- $C_{1-6}$ alkylamino group such as methylamino, ethylamino, dimethylamino, etc.), amidino group, acyl group (e.g. a $C_{1-6}$ alkanoyl group such as formyl, acetyl, propionyl, etc.), carbamoyl group, a mono- or di-lower alkyl carbamoyl group (e.g. a mono- or di- $C_{1-6}$ alkylcarbamoyl group such as methylcarbamoyl, ethylcarbamoyl, dimethylcarbamoyl, etc.), sulfamoyl group, a mono- or di-lower alkylsulfamoyl group (e.g. a mono- or di- $C_{1-6}$ alkylsulfamoyl group such as methylsulfamoyl, ethylsulfamoyl, dimethylsulfamoyl, etc.), carboxyl group, a lower alkoxycarbonyl group (e.g. a $C_{1-6}$ alkoxy-carbonyl group such as methoxycarbonyl, ethoxycarbonyl, etc.), hydroxyl group, a lower alkoxy group (e.g. a $C_{1-6}$ alkoxy group such as methoxy, ethoxy, etc.), a lower alkenyloxy group (e.g. a $C_{2-6}$ alkenyloxy group such as allyloxy, 2-butenyloxy, etc.), carbamoyloxy group, mercapto group, a lower alkylthio group (e.g a $C_{1-6}$ alkylthio group such as methylthio, ethylthio, etc.), sulfo group, cyano group, azido group, and halogen (e.g. fluorine, chlorine, bromine, etc.). The number of these substituents is preferably 1 to 3, and, when the number is plural, the substituents may be the same as or different from one another. Preferable examples of $R^3$ include hydrogen atom or a lower alkyl group (e.g. a $C_{1-6}$ alkyl group such as methyl, ethyl, propyl, t-butyl, etc.) optionally substituted with one or two of an amino group, a hydroxyl group, a carbamoyl group, vinyl group, cyano group, a carboxyl group, a lower alkoxycarbonyl group (e.g. a $C_{1-6}$ alkoxy-carbonyl group such as methoxycarbonyl, ethoxycarbonyl, etc.) and a mono- or di-lower alkylcarbamoyl group (e.g. a mono- or di- $C_{1-6}$ alkyl-carbamoyl group such as methylcarbamoyl, ethylcarbamoyl, dimethylcarbamoyl, etc.). Preferable examples of $R^4$ and $R^{4'}$ include a hydrogen atom or a lower alkyl group (e.g. a $C_{1-6}$ alkyl group such as methyl, ethyl, propyl, etc.) which may be substituted with one or two substituents selected from the group consisting of an amino group, a hydroxyl group, a carbamoyl group and cyano group.

The Compound (I) or Compound (I') or a salt thereof has excellent effects in the case where has an acylamino group at the 7-position of the cephem nucleus. As the acyl group of the acylamino group, mention is made of any acyl group as substituted on the 6-position amino group of known penicillin derivatives or any acyl group as substituted on the 7-position amino group of known cephem compounds. Preferable examples of the acyl group include a group of the formula (V):

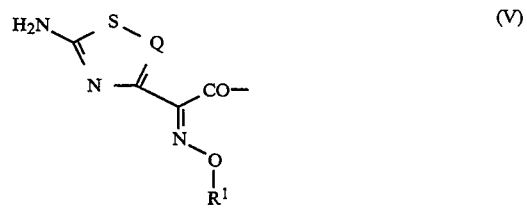

wherein each symbol is as defined above, a group of the formula (VI):

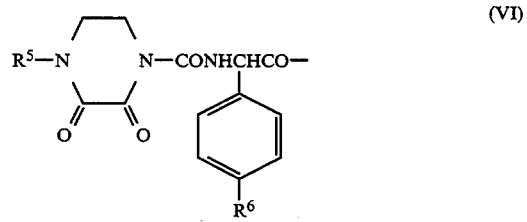

wherein $R^5$ stands for a lower alkyl group and $R^6$ stands for a hydrogen atom or a hydroxyl group, and a group of the formula (VII):

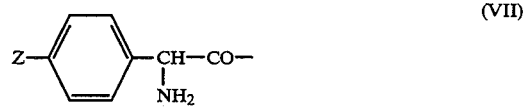

wherein Z stands for a hydrogen atom, a halogen or a hydroxyl group.

Among them, groups (V) are especially preferable. In other words, preferable examples of the Compound (I) or salt thereof are compounds represented by the formula (III):

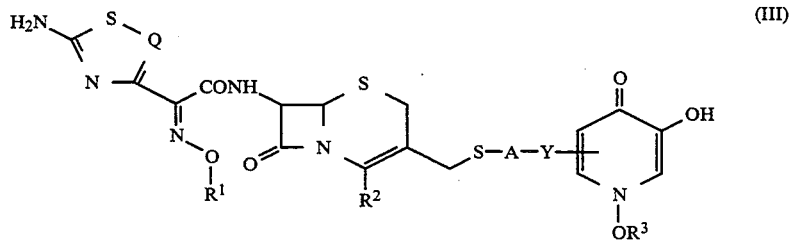

or the formula (IV):

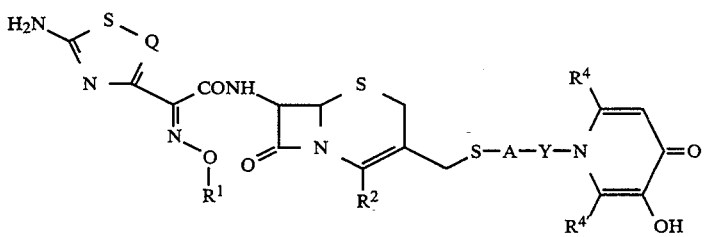

wherein each symbol is as defined above, or salts thereof.

In the above formulae, $R^1$ stands for hydrogen atom or an optionally substituted hydrocarbon group. Examples of the hydrocarbon group shown by $R^1$ include lower alkyl, lower alkenyl, lower alkynyl, cycloalkyl, aralkyl and aryl groups. The lower alkyl groups include straight-chain or branched, preferably, $C_{1-6}$ alkyl groups, exemplified by methyl, ethyl, n-propyl, isopropyl, n-butyl, isobutyl, sec-butyl, tert-butyl, n-pentyl, n-hexyl, etc. The lower alkenyl groups include straight-chain or branched, preferably, $C_{2-6}$ alkenyl groups, exemplified by allyl, propenyl, butenyl, pentenyl, etc. The lower alkynyl groups include straight-chain or branched, preferably, $C_{2-6}$ alkynyl groups, exemplified by propinyl, butynyl, pentynyl, etc. The cycloalkyl groups are preferably $C_{3-6}$ cycloalkyl groups, exemplified by cyclopropyl, cyclobutyl, cyclopentyl, cyclohexyl, etc. The aralkyl groups are preferably $C_{7-10}$ aralkyl groups, exemplified by benzyl group. The aryl groups include $C_{6-10}$ aryl groups, exemplified by phenyl group, etc. The hydrocarbon groups shown by $R^1$ may be substituted with 1 to 3 of substituents selected from the group consisting of, a carboxyl group, a $C_{1-6}$ alkoxycarbonyl group (e.g. methoxycarbonyl, ethoxycarbonyl, etc.), a carbamoyl group, a $C_{1-6}$ alkylthio group (e.g. methylthio, ethylthio, etc.), a sulfamoyl group, an amino group, a hydroxyl group, cyano group, a carbamoyloxy group and a halogen (e.g. fluorine, chlorine, etc.). Among them, preferable $R^1$ includes hydrogen atom and a lower alkyl group (e.g. $C_{1-6}$ alkyl group such as methyl, ethyl, propyl, etc.) optionally substituted with one or two substituents selected from the group consisting of a lower alkyl group (e.g. $C_{1-6}$ alkyl group such as methyl, ethyl, propyl, etc.), fluorine and carboxyl group.

In the above formulae, Q stands for N, CH, CCl or CF, $R^5$ stands for a lower alkyl group (e.g. $C_{1-6}$ alkyl group such as methyl, ethyl, propyl, etc ), $R^6$ stands for hydrogen atom or a hydroxyl group, and Z stands for hydrogen atom, a halogen (e.g. fluorine, chlorine, bromine, etc.), respectively.

In the above formulae, $R^2$ stands for an optionally esterified carboxyl group represented by the formula:

—COOR wherein R stands for hydrogen atom or an ester residue, and, as the ester residue (R) of the carboxyl group, use is made of, for example, a group represented by the formula:

$$-\underset{R^7}{\underset{|}{CH}}OCOR^8$$

(wherein $R^7$ stands for hydrogen atom, an alkyl group, a cycloalkyl group or a cycloalkylalkyl group; and $R^8$ stands for hydrogen atom, an alkyl group, a cycloalkyl group, an alkoxy group, a cycloalkyloxy group, a cycloalkylalkyl group, an alkenyloxy group or phenyl group), phthalidyl group, (2-oxo-5-methyl-1,3-dioxol-4-yl)methyl group, an alkoxyalkyl group, an alkylthioalkyl group, tert-butyl group, 2,2,2-trichloroethyl group, benzyl group, p-methoxybenzyl group, p-nitrobenzyl group, benzhydryl group, trityl group, trimethylsilyl group, allyl group, etc. As the alkyl group in the above-mentioned alkyl group as well as cycloalkylalkyl, alkoxyalkyl group and alkylthioalkyl group, use is made of, for example, $C_{1-6}$ straight-chain or branched alkyl groups (e.g. methyl, ethyl, propyl, isopropyl, butyl, 2,2-dimethylpropyl, etc.), and, as the cycloalkyl group in the above-mentioned cycloalkyl group and cycloalkyloxy group or cycloalkylalkyl group, use is made of, for example, $C_{3-7}$ cycloalkyl groups (e.g. cyclopropyl, cyclobutyl, cyclopentyl, cyclohexyl, cycloheptyl, etc.). As the alkoxy group in the above-mentioned alkoxy group and alkoxyalkyl group, use is made of, for example, $C_{1-10}$ straight-chain or branched alkoxy groups (e.g. methoxy, ethoxy, propoxy, isopropoxy, butoxy, hexyloxy, decyloxy, etc.). And, as the alkenyloxy group, use is made of, for example, $C_{2-7}$ straight-chain or branched alkenyloxy groups (e.g. allyloxy, etc.). As an especially preferable ester residue, use is made of a group giving a biologically unstable ester derivative which is suitable for oral administration. Preferable examples of the group include acetoxymethyl group, 1-acetoxyethyl group, 1-acetoxypropyl group, pivaloyloxymethyl group, 1-isopropyloxycarbonyloxyethyl group, 1-cyclohexyloxycarbonyloxyethyl group, phthalidyl group and (2-oxo-5-methyl-1,3-dioxol-4-yl)methyl group.

Among the Compound (I) or Compound (I') or salts thereof, a compound represented by the following formula ($I_1$) or a salt thereof is preferable.

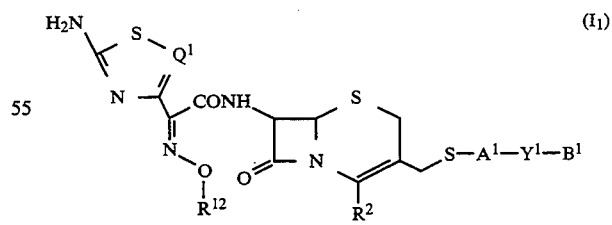

wherein $Q^1$ stands for N or CH; $R^{12}$ stands for hydrogen atom or a $C_{1-6}$ alkyl group (e.g., methyl, ethyl, propyl, etc.) optionally substituted with a $C_{1-4}$ alkoxy (e.g., methoxy, ethoxy) or a carboxyl; $R^2$ stands for an optionally esterified carboxyl group; $A^1$ stands for a divalent group formed by eliminating two hydrogen atoms from thiazole, isothiazole, thiadiazole, triazole or tetrazole; $Y^1$ stands for —$CH_2$—, —$CH_2CH_2$—, —S—$CH_2$— or —NHCO—CH$_2$—; B$^1$ stands for a group of the formula:

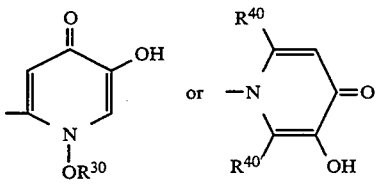

wherein R$^{30}$, R$^{40}$ and R$^{40'}$ each stand for hydrogen atom or a C$_{1-4}$ alkyl group (e.g., methyl, ethyl) optionally substituted with a hydroxyl.

Among them, compounds represented by the formula (I$_1$) or salts thereof wherein the symbols show the following groups are more preferable.

Q$^1$: N

R$^{12}$: a C$_{1-4}$ alkyl group (e.g. methyl, ethyl, propyl) optionally substituted with a carboxyl A$^1$: 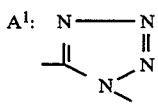

Y$^1$: —CH$_2$—

B$^1$: 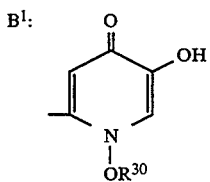

R$^{30}$: H or methyl

As salts of the object Compound (I) or Compound (I') of this invention, use is preferably made of pharmaceutically acceptable ones exemplified by salts with an inorganic base, salts with an organic base, salts with an inorganic acid, salts with an organic acid, or salts with a basic or acidic amino acid. Preferable salts with an inorganic base are exemplified by alkali metal salts such as sodium salts or potassium salts; alkaline earth metal salts such as calcium salts or magnesium salts; and aluminum salts. Preferable salts with an organic base are exemplified by salts with trimethylamine, triethylamine, pyridine, picoline, ethanolamine, diethanolamine, dicyclohexylamine or N,N'-dibenzylethylenediamine. Preferable examples of salts with an inorganic acid include salts with hydrochloric acid, hydrobromic acid, nitric acid, sulfuric acid, phosphoric acid or the like. Preferable examples of salts with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toleuenesulfonic acid or the like. Preferable examples of salts with a basic amino acid include salts with arginine, lysine, ornithine or the like, and preferable examples of salts with an acidic amino acid include salts with aspartic acid, glutamic acid or the like. Among these salts, salts with a base (i.e. salts with an inorganic base, salts with an organic base, salts with a basic amino acid) mean salts which can be formed in the case where the Compound (I) or (I') has an acid group or groups, i.e. carboxyl group at the 4-position of the cephem nucleus or/and carboxyl group in an acyl group at the 7-position (e.g. R$^1$), A or/and B, and, salts with an acid (i.e. salts with an inorganic acid, salts with an organic salt, salts with an acidic amino acid) means salts which can be formed in the case where the Compound (I) or (I') has a basic group or groups such as amino group in an acyl group at the 7-position (e.g. R$^1$), A or/and B.

The Compound (I) or (I') or salts thereof are valuable antibiotics showing excellent antimicrobial activities against Gram-positive and Gram-negative bacteria including clinically isolated strains and can be used as medicines for man and domestic animals (e.g., dog, cat, rat, mouse, etc.), thus being used safely as an antimicrobial agent for the therapy and prophylaxis of infections caused by various bacteria. And, the Compound (I) or (I') or salts thereof are remarkably low in toxicity and undesirable side effects, while the concentration thereof in blood, after administration, being maintained high for a long period of time (having excellent durability).

The object Compound (I) or (I') or salts thereof of the present invention can be administered orally or non-orally, in combination with a pharmaceutically acceptable carrier, as a solid preparation such as tablets, capsules, granules or powder; or as a liquid preparation such as syrup or injection.

As a pharmaceutically acceptable carrier, use is made of various organic or inorganic carriers conventionally employed in the preparation of pharmaceutical formulations. In solid preparations, are adequately incorporated excipients, lubricants, binders and disintegrators, while, in liquid preparations, are adequately incorporated solvents, solubilizers, suspending agents, isotonizing agents, buffer agents, pain-lessening agents, etc. And, upon necessity, such additives as preservatives, anti-oxidants, coloring agents, sweetening agent, etc. may be employed in accordance with a conventional manner. Preferable examples of excipients include lactose, sucrose, D-mannitol, starch, crystalline cellulose, soft silicic acid anhydride, etc. Preferable lubricants are exemplified by magnesium stearate, calcium stearate, talc and colloid silica. Preferable binders are exemplified by crystalline cellulose, sucrose, D-mannitol, dextrin, hydroxypropyl cellulose, hydroxypropyl methylcellulose and polyvinylpyrrolidone. Preferable disintegrators are exemplified by starch, carboxymethylcellulose, carboxymethylcellulose calcium, cross carmellose sodium and carboxymethyl starch sodium. Preferable solvents are exemplified by injectable water, alcohol, propylene glycol, macrogol, sesame oil and corn oil. Preferable solubilizers are exemplified by polyethylene glycol, propylene glycol, D-mannitol, benzyl benzoate, ethanol, trisaminomethane, cholesterol, triethanolamine, sodium carbonate and sodium citrate. Preferable examples of suspending agents include surfactants such as stearyl triethanolamine, sodium laurylsulfate, laurylaminopropionic acid, lecithin, benzalkonium chloride, benzethonium chloride and monostearic acid glycerin; and hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose. Preferable isotonizing agents are exemplified by sodium chloride, glycerin and D-mannitol. Preferable buffer agents are exemplified by phosphate, acetate, carbonate and citrate. Preferable examples of pain-lessening agents include benzyl alcohol. Preferable examples of preservatives include para-hydroxybenzoic acid esters, chlorobutanol, benzyl alcohol, phenethyl alcohol, tetrahydroacetic acid and sorbic acid. Preferable anti-oxidants are exemplified by sulfite and ascorbic acid. Further, it is also possible to provide a preparation showing antimicrobial activities of broader spectrum in admixture with any other active components (e.g. β-lactam antibiotics).

The Compounds (I) or (I') or salts thereof can be used, as therapeutic agents of bacterial infections, for the therapy and prophylaxis of, for example, respiratory infections, urinary tract infections, suppurative diseases, bile tract infections, intestinal infections, gynecological infections, oto-rhinolaryngological infections, surgical infections or the like in man and other mammals. The dosage of the Compound (I) or (I') or a salt thereof for one day varies with the conditions, body weight of the patient or the route of administration, and, for non-oral administration, it ranges from about 0.5 to 80 mg, preferably from about 2 to 40 mg, of the active component (the Compound (I) or a salt thereof) per kilogram of body weight of an adult human, which can suitably be administered daily in the form of intravenous or intramuscular injection once a day or divided into two doses. And, for oral administration to an adult patient, the suitable daily dosage ranges from about 1 to 100 mg, preferably about from 2.5 to 50 mg of the active component (the Compound (I) or (I') or a salt thereof) per kilogram of body weight, once a day or divided into two doses.

The Compounds (I) or salts thereof can be produced by, for example, Preparation Methods 1 to 3 set forth as follows.

PREPARATION METHOD 1

The Compound (I) or a salt thereof can be produced by reacting a cephem compound having a substituent at the 3-position of the cephem nucleus, which is represented by the formula (VIII):

$$-CH_2-R^{10} \qquad (VIII)$$

wherein $R^{10}$ stands for a hydroxyl group, an acyloxy group or a halogen (hereinafter simply referred to as "compound (IX)") or a salt thereof, with a compound represented by the formula (X):

$$HS-A-Y-B \qquad (X)$$

wherein each symbol is as defined above, or a salt thereof.

In the case where the compounds (IX) or (X) or salts thereof contain reactive groups such as amino group, hydroxyl group or carboxyl group, these groups may be those protected by a conventional manner with protective groups set forth below in the compounds (XII) and (XIII), and these protecting groups can be removed, upon necessity, after the reaction by a conventional manner.

As salts of the compound (IX), use is made of, for example, those with bases capable of accelerating the reaction or neutralizing the resulting acid or assisting in dissolving the materials. As these bases, use is made of, for example, tertiary amines such as triethylamine, tributylamine, diisopropylethylamine, etc. or alkali metal hydrogencarbonates such as sodium hydrogencarboante, potassium hydrogencarbonate, etc., among others. These bases may be added to the reaction mixture together with the compound (IX) for the purpose stated above. The amount ranges, in general, preferably from about 1 to 5 times as much mol.relative to the compound (IX). As salts of the compound (X), use is made of, for example, inorganic acid addition salts such as hydrochloride, hydrobromide, sulfate, nitrate and phosphate; organic acid addition salts such as formate, acetate, trifluoroacetate, methanesulfonate and p-toluenesulfonate; organic base addition salts such as triethylamine salt and tributylamine salt; and inorganic base addition salts such as sodium salt and potassium salt.

(1): in the case where $R^{10}$ stands for a hydroxyl group—

In this reaction, the compound (X) or a salt thereof is used in an amount ranging from about 1 to 10 mols, preferably from about 1 to 5 mols relative to 1 mol of the compound (IX) or a salt thereof. The reaction is usually conducted in an organic solvent which does not hamper the reaction. As the organic solvent which does not hamper the reaction, use is made of, for example, amides such as formamide, dimethylformamide and dimethylacetamide; halogenated hydrocarbons such as dichloromethane, chloroform and 1,2-dichloroethane; ethers such as diethyl ether, tetrahydrofuran and dioxane; esters such as methyl acetate, ethyl acetate, isobutyl acetate and methyl propionate; nitriles such as acetonitrile and propionitrile; nitro compounds such as nitromethane and nitroethane; ketones such as acetone and methylethylketone; aromatic hydrocarbons such as benzene and toluene. These solvents may be used singly or in a mixture of two or more of them in a suitable ratio. Especially preferable ones include, for example, dichloromethane, tetrahydrofuran, acetonitrile, formamide, dimethylformamide, etc., or a mixture solvent of dimethylformamide and acetonitrile, a mixture solvent of dichloromethane and acetonitrile, a mixture solvent of dichloromethane and tetrahydrofuran, etc.

For accelerating this reaction, for example a cyclic phosphorus compound described in U.S. Pat. No. 4,642,365 or phosphorous ester can be employed. More specifically stating, for example, a cyclic phosphorus compound represented by the formula (XI):

wherein $R^{11}$ stands for phenyl group or a lower alkoxy group, may be used for accelerating this reaction. As the lower alkoxy group represented by $R^{11}$ in the general formula (XI), use is made of, for example, a $C_{1-4}$ alkoxy group such as methoxy, ethoxy, propoxy, butoxy or isobutoxy. Among the cyclic phosphorus compounds (XI), are preferable, for example, methyl o-phenylenephosphate, ethyl o-phenylenephosphate and 2-phenyl-2-oxo-1,3,2-benzodioxaphosphor, among others. The compound (XI) is used in a range of from about 1 to 10 mols, preferably from about 1 to 6 mols relative to one mol. In the case of using the compound (XI), it is preferable, for example, to react the compound (IX) or a salt thereof, the compound (X) or a salt thereof and the compound (XI) in an organic solvent mentioned above. More specifically, the compound (IX) or a salt thereof and the compound (X) or a salt thereof are mixed in an organic solvent, to which is then added the compound (XI) or its solution in an organic solvent, or the compound (X) or a salt thereof and the compound (XI) are mixed in an organic solvent, to which is then added the compound (IX) or a salt thereof or its solution in an organic solvent, to thereby achieve this reaction.

While the reaction temperature varies with the amount, kinds and any other factors of the starting compound (IX) or a salt thereof, the compound (X) or a salt thereof, the cyclic phosphorus compound (XI), the organic solvent, the base, etc. then employed, it usually ranges from about −80° to 60° C. The reaction time ranges from about 1 minute to 24 hours.

(2): in the case where $R^{10}$ stands for an acyloxy group—

As the acyloxy group, use is made of, for example, a $C_{1-6}$ alkanoyloxy group (e.g., acetoxy, propyloxy, etc.) which is optionally substituted with a halogen (e.g., Cl, Br, etc.), phenyl or a $C_{1-6}$ alkanoyl (e.g., acetyl, etc.), etc. such as acetoxy, acetoacetoxy, dichloroacetoxy, etc.

In this reaction, the compound (X) or a salt thereof is employed in an amount usually ranging from about 1 to 5 mols, preferably form about 1 to 3 mols, relative to one mol of the compound (IX) or a salt thereof. The reaction is conducted usually in water or a mixed solvent of water and a water-miscible organic solvent, or an organic solvent which does not exert undesirable effects on the reaction.

When the reaction is carried out in water or a mixed solvent of water and a water-miscible organic solvent (e.g. ketones such as acetone, alcohols such as methanol and ethanol, and nitriles such as acetonitrile), it is advantageous to conduct the reaction at a pH ranging from 2 to 8, preferably around neutral pH, i.e. 5 to 8. The reaction is conducted at temperatures ranging from about 10 to 100° C., preferably about 30° to 80° C. While the reaction time varies with the reaction temperatures then employed, it ranges usually from 10 minutes to 70 hours.

On the other hand, when an organic solvent is employed, the reaction may be conducted, for the purpose of accelerating the reaction, in the presence of an acid, an acid addition product, or water and a halogenated phosphorus compound. Preferable examples of the acid include boron trifluoride and methanesulfonic acid, preferable examples of the acid addition product include boron trifluoride etherate, and, as preferable halogenated phosphorus compound, use is made of diphosphoryl tetrachloride, dichlorophosphoric acid, etc. Preferable organic solvents include, for example, ethers, halogenated hydrocarbons, ketones and nitriles, which are described above for the reaction in the case of $R^{10}$=a hydroxyl group. The reaction is conducted at temperatures ranging from −40° C. to 100° C. preferable from −20° to 80° C. While the reaction time varies with the reaction temperatures, it ranges from 10 minutes to 70 hours.

(3): in the case where $R^{10}$ stands for a halogen—

This reaction is preferably conducted in a solvent. Preferable solvents include, besides ethers, esters, halogenated hydrocarbons, aromatic hydrocarbons, amides, ketones and nitriles as described in reference to the reaction in the above-mentioned case of $R^{10}$=a hydroxyl group, water or alcohols such as methanol, ethanol, propanol, etc. The compound (X) or a salt thereof is usually employed in an amount ranging from about 1 to 5 mols, preferably from about 1 to 3 mols, relative to 1 mol of the compound (IX) or a salt thereof. The reaction is conducted at temperatures ranging from about −10° to 100° C., preferably from about 20° to 60° C. The reaction time ranges usually from about 30 minutes to 15 hours, preferably from 1 to 5 hours. For accelerating the reaction, the reaction can be conducted in the presence of a dehydrohalogenating agent, as exemplified by inorganic bases such as sodium carbonate, potassium carbonate, sodium hydrogencarbonate and potassium hydrogencarbonate; tertiary amines such as triethylamine, tripropylamine, tributylamine, diisopropylethylamine, cyclohexyldimethylamine, N,N-dimethylaniline, N-methylpiperidine, N-methylpyrrolidine and N-methylmorpholine; pyridines such as pyridine, picoline, lutidine and collidine; alkylene oxides such as propylene oxide and epichlorohydrin, among others. And, the compound (X) or a salt thereof itself may be used to act as the dehydrohalogenating agent as well. In this case, the compound (X) is used in an amount of two or more mols relative to one mol of the compound (IX) or a salt thereof. The halogen represented by $R^{10}$ include chlorine, bromine, iodine, among which iodine is preferable. The compound (IX), in which $R^{10}$ stands for a halogen, or a salt thereof can be readily produced by the method described in EP-A-76466 or an analogous method thereto.

And, the compound (X) can be produced by, for example, reacting a compound represented by the formula:

HS—A—P with a compound represented by the formula:

Q'—B (wherein P and Q' stand for groups which react with each other to form Y; and Y, A and B are as defined above), in a ratio of equimol in a solvent such as amide, e.g. formamide, dimethylformamide, etc. The reaction temperature ranges from about −10° to 100° C., and the reaction temperature ranges usually from about 30 minutes to 15 hours. Further, the compound (X) can be readily produced also by methods described in, for example, "Chemistry of Heterocyclic Compounds" (John Wiley & Sons,) or "Adv. Heterocycl. Chem." (Academic Press). And, the compound (X) can be produced also by methods described in the following Reference Examples or analogous methods thereto.

PREPARATION METHOD 2

And, Compound (I) having, at the 7-position of the cephem nucleus, an acylamino group, or a salt thereof can be produced also by subjecting Compound (I) having, at the 7-position, amino group, or a salt thereof to acylation to be employed for the production of conventional cephem derivatives. Preferable acylating agents include those to be employed for the production of conventional cephem derivatives. For example, the Compound (I) or a salt thereof, especially a compound (III), (IV) or a salt thereof can be produced by reacting a compound represented by the formula (XII):

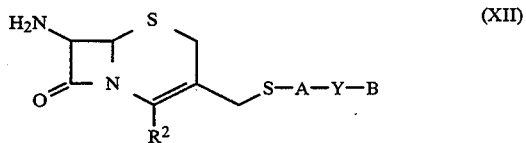

wherein each symbol is as defined above, or a salt thereof, with a compound represented by the formula (XIII):

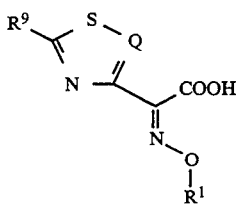

wherein R⁹ stands for an optionally protected amino group; Q and $R^1$ are as defined above, or a salt thereof or a reactive derivative at its carboxyl group, followed by, upon necessity, removing the protecting group.

In cases where amino group, hydroxyl group or carboxyl group is present in substituents shown by $R^1$, A and B, in the formulae (XII) and (XIII), it is preferable that these groups are protected with protecting groups. As protecting groups of this amino group (including protecting groups to be employed for $R^9$), use is suitably made of, those to be employed in the fields of, for example, β-lactam and peptide. Among them, preferable ones include formyl, chloroacetyl, tert-butoxycarbonyl, benzyloxycarbonyl, p-methoxybenzyloxycarbonyl, p-nitrobenzyloxycarbonyl, 2-trimethylsilylethoxycarbonyl, 2,2,2-trichloroethoxycarbonyl and trityl. And, in the case where hydroxyl group is present, this hydroxyl group is preferably protected. As protecting groups of this hydroxyl group, use is made of, for example, chloroacetyl, benzyl, p-nitrobenzyl, methylthiomethyl, methoxymethyl, trimethylsilyl, tert-butyl dimethylsilyl, 2-tetrahydropyranyl and 4-methoxy-4-tetrahydropyranyl. Further, in the case where carboxyl group is present, this carboxyl group is preferably protected. As protecting groups of the carboxyl group, use is made of benzyl, benzhydryl, trityl, p-methoxybenzyl, p-nitrobenzyl, tert-butyl, etc. As salts of the compound (XII), use is made of, for example, those with, the same bases as mentioned in the salts of the compound (IX). These bases may be added together with the compound (XII), and the amount of the bases to be added ranges usually from about 1 to 10 times as much mols, preferably from about 1 to 5 times as much mols relative to the compound (XII). As salts of the compound (XIII), use is made of, for example, alkali metal salts such as sodium salts or potassium salts; alkaline earth metal salts such calcium salts or magnesium salts; salts with an organic base such as trimethylamine, triethylamine, pyridine, picoline, ethanolamine, diethanolamine, dicyclohexylamine or N,N'-dibenzylethylenediamine.

As the reactive derivatives at the carboxyl group of the compound (XIII), use is made of, for example, acid halides, acid anhydrides, active amides, active esters and active thioesters which can be prepared in accordance with conventional means. These reactive derivatives are specifically described as follows.

1) Acid halides: For example, acid chloride, acid bromide or the like are used.
2) Acid anhydrides: For example, mixed anhydrides with mono-lower alkyl carbonate are used.
3) Active amides: For example, amides formed with pyrazole, imidazole, 4-substituted imidazole, dimethylpyrazole, benzotriazole, etc. are used.
4) Active esters: For example, esters such as methoxymethyl ester, benzotriazole ester, 4-nitrophenyl ester, 2,4-dinitrophenyl ester, trichlorophenyl ester, pentachlorophenyl ester, etc., as well as esters formed with 1-hydroxy-1H-2-pyridine, N-hydroxysuccinimide, N-hydroxyphthalimide, etc. are used.
5) Active thioesters: For example, thioesters formed with heterocyclic thiols such as 2-pyridylthiol, 2-benzothiazolylthiol, etc. are used.

In this reaction, the compound (XIII) or a salt thereof or a reactive derivative at its carboxyl group is used 1 mol or more, preferably about in the proportion of 1 mol to 4 mol, relative to 1 mol of the compound (XII) or a salt thereof. This reaction is conducted usually in a solvent. Examples of the solvent include water, ketones such as acetone, etc., ethers such as tetrahydrofuran, dioxane, etc., nitriles such as acetonitrile, etc., halogenated hydrocarbons such as dichloromethane, chloroform, 1,2-dichloroethane, etc., esters such as ethyl acetate, etc., and amides such as dimethylformamide, dimethylacetamide, etc. These solvents may be used singly or in combination of two or more of them in a suitable mixture ratio. When the compound (XIII) is used as the free acid or as its salt, the reaction is conducted preferably in the presence of a condensing agent. Examples of the condensing agent include N,N'-dicyclohexylcarbodiimide, N-cyclohexyl-N'-morpholinoethylcarboxiimide, N-cyclohexyl-N'-(4diethylaminocyclohexyl)carbodiimide, N-ethyl-N'-(3dimethylaminopropyl)-carbodimide, etc. The reaction can also be carried out in the presence of a base which includes, for example, alkali metal carbonates such as sodium carbonate, potassium carbonate, sodium hydrogencarbonate, potassium hydrogencarbonate, etc., tertiary amines such as triethylamine, tributylamine, N-methylmorpholine, N-methylpiperidine, N,N-dimethylaniline, etc., and pyridines such as pyridine, picoline, lutidine, colidine, etc. These bases serve to accelerate the reaction, to neutralize the acid formed during the reaction or to make the starting materials readily soluble, and are used in an amount ranging usually from about 0.01 to 10 times as much mols, preferably from about 0.1 to 5 times as much mols, relative to the compound (XII) or a salt thereof. The reaction temperature is not specifically limitative, but it ranges usually from about −30° to 50° C. The reaction time ranges from several minutes to about several ten hours (e.g. 5 minutes to 30 hours).

PREPARATION METHOD 3

Furthermore, the compound (III) or (IV), in which Q stands for CH, or a salt thereof can be produced by reacting a compound represented by the formula (XIV):

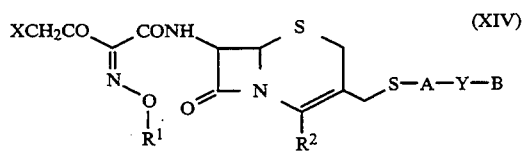

wherein $R^1$, $R^2$, A, B and Y are as defined above, and X stands for a halogen, or a salt thereof, with thiourea.

The group X in the compound (XIV) stands for a halogen, e.g. chlorine, bromine, iodine, etc. As salts of the compound (XIV), use is also made of the same ones as those of the compound (IX) described in the above Preparation Method 1 (inorganic base salts, ammonium salts, organic base salts, etc.). This reaction is conducted usually in a solvent. As the solvent, use is made of the above-mentioned ethers, alcohols, amides, etc. Thiourea is used in an amount ranging usually from about 1 to 5 mols, preferably from about 1 to 3 mols, relative to 1 mol of the compound (XIV) or a salt thereof. The reaction is carried out in a temperature range from about 0° to 100° C., preferably from about 20° to 60° C. The reaction time ranges usually from 30 minutes to 6 hours, preferably from 1 to 5 hours.

The Compounds (I') or salts thereof can be produced by using the corresponding starting material according to the above-mentioned Preparation Methods 1 to 3.

The starting compound (XIV) or a salt thereof can be easily produced by reacting a compound represented by the formula (XV):

wherein symbols are as defined above, or a salt thereof or a reactive derivative thereof, with the above-mentioned compound (XII) or a salt thereof in accordance with the method of acylation described in Preparation Method 2.

And, other starting compounds represented by (XII), (XIII) and (XV) or salts or reactive derivatives thereof can be easily produced by per se known methods (e.g. U.S. Pat. No. 4,317,907, U.S. Pat. No. 4,446,318, U.S. Pat. No. 4,098,888, EP-A-246,603, etc.) or methods analogous thereto.

The reaction products obtained by the above-mentioned Preparation Methods 1 to 3 can be isolated and purified by known means, for example, solvent extraction, change of pH, phasic transfer, salting out, crystallization, recrystallization, chromatography, etc. And, in the case where a protecting group is included in the reaction product, the protecting group is, when necessary, removed by a conventional method, to thereby obtain the Compound (I) or (I') or its salt. In the field of synthesis of β-lactam and peptides, hydroxyl- or carboxyl-protecting groups have been exhaustively studied, and hence protection and de-protection methods have been established. For example, the de-protection method can be conveniently selected from known methods using acids, bases, hydrazine, reduction or sodium N-methyldithiocarbamate.

When the compound isolated as above is a free acid or a free base, it can be converted to a corresponding pharmacologically acceptable salt or ester in accordance with a conventional manner, and, when the compound isolated as above is a salt or ester, it may optionally be converted to a corresponding free acid or free base in accordance with a conventional manner. These conversions can be conducted before or after the removal of the above-mentioned protecting groups.

In the above-mentioned Preparation Methods 1 to 3, the Compound (I) or (I') or a salt thereof may in some case (e.g. of the Compound (III) or (IV) or a salt thereof) be obtained as a mixture of the syn(Z)-isomer and anti[E]-isomer. For isolating the desired syn-isomer (i.e. the Compound (I) or (I') or a salt thereof) from the mixture, a per se conventional means or an analogous one thereto can be resorted to, as exemplified by separation utilizing the difference in solubility, crystallizability, etc. or isolation by means of chromatography.

By the following Reference Examples and Examples, the present invention will be illustrated in further detail. They are, however, mere examples, and do not limit the invention whatsoever.

Elution in a column chromatography in the following Reference Examples and Examples was conducted while monitoring with TLC (Thin Layer Chromatography). In the TLC monitoring, the TLC plate used was 60F$_{254}$ manufactured by E. Merck AG., the developing solvent was the same as the one used for eluting in the column chromatography, and the detection was conducted with a UV detector. The silica gel for the column was Kieselguhr 60 (70–230 mesh) manufactured by E. Merck AG. Sephadex LH-20 is a product of Pharmacia Fine Chemicals. Amberlite XAD-II resin is a product of Rohm & Hass Co. HP-20 and SP-207 resin are products of Mitsubishi Chemical Industries, Ltd.. LiCroprep RP-18 is a product of Merck & Co., Inc. NMR spectra were measured using tetramethylsilane or 3-(trimethylsilyl)propionic acid-2,2,3,3-d$_4$ sodium salt as an internal or external standard with a spectrometer Gemini 200 (200 MHz), and all delta values are expressed in ppm. The value shown in ( ) for a mixed solvent is a mixing ratio in volume of constituent solvents. The percent (%) for a mixed solvent indicates the percent by volume. And, while the term "room temperature" in the Examples means, in general, a temperature range of about 15° C. to 30° C., said term in Reference Examples and Examples means 25° C.

The symbols in Reference Examples and Examples have the following meaning.

s: singlet
brs: broad singlet
brd: broad doublet
d: doublet
t: triplet
q: quartet
ABq: AB type quartet
dd: double doublet
m: multiplet
br.: broad
J: coupling constant
ml: milliliter
CDCl$_3$: deuterochloroform
DMSO: dimethyl sulfoxide
Hz: Herz
D$_2$O: deuterium oxide
CFU: colony forning unit
g: gram
mg: milligram
μg: microgram

REFERENCE EXAMPLE 1

In ethanol (45 ml) was suspended 1,5-bis(diphenylmethoxy)-2-phthalimidomethyl-4-pyridone (3.77 g). To the suspension was added hydrazine hydrate (0.23 ml), and the mixture was heated for 1.5 hour under reflux. The reaction mixture was cooled, then insolubles were filtered off. The filtrate was concentrated, to which was added chloroform (30 ml). Insolubles were filtered off, and the filtrate was concentrated to dryness. The concentrate was dissolved in ethanol (20 ml), to which was added water (2 ml). To the mixture were added, under ice-cooling, triethylamine (0.37 ml) and carbon disulfide (0.34 ml). The mixture was stirred for 2 hours at room temperature, to which was added methyl iodide (0.35 ml), followed by stirring for 30 minutes at room temperature. Resulting crystalline precipitates were collected by filtration to give 1.26 g of 1,5-bis(diphenylmethoxy)-2-methylthiothiocarbonylaminomethyl-4pyridone, m.p. 176°-178° C. IR(KBr): 1620, 1575 cm$^{-1}$. $^1$H-NMR(CDCl$_3$) ε: 2.59(3H,s), 4.66(2H,d,J=5 Hz), 5.84(1H,s), 6.13(1H,s), 6.70(1H,s), 7.2-7.4(20H,m), 9.73(1H,brs)

REFERENCE EXAMPLE 2

The compound obtained in Reference Example 1 (1.0 g) was suspended in water (40 ml). To the suspension were added sodium azide (0.37 g) and ethanol (20 ml), and the mixture was heated overnight under reflux. Insolubles were filtered off, and the filtrate was washed with ethyl acetate, then the pH was adjusted to 3 with phosphoric acid, followed by extraction with ethyl acetate. The extract solution was dried over anhydrous magnesium sulfate, which was concentrated to dryness under reduced pressure. The concentrate was purified by means of a silica gel column chromatography (eluent: acetonitrile-methanol 9:1) to give 0.23 g of 1-[(1-diphenylmethoxy-5-hydroxy-4-pyridon-2-yl)methyl-]5-mercapto-1H-tetrazole. IR(KBr): 1620, 1520 cm$^{-1}$. $^1$H-NMR(DMSO-d$_6$) ε: 5.37(2H,s), 6.46(1H,s), 6.70(1H,s), 7.2-7.6(21H,m), 8.07(1H,s)

REFERENCE EXAMPLE 3

2,5-Dimercapto-1,3,4-thiadiazole (549 mg) was dissolved in dimethylformamide (hereinafter abbreviated as DMF) (11 ml). To the solution were added, while stirring under ice-cooling, triethylamine (1.53 ml) and 2-chloromethyl-1,5-bis(diphenylmethoxy)-4-pyridone (1.86 g). The reaction mixture was stirred for one hour at the same temperature, diluted with water (50 ml), then subjected to extraction with ethyl acetate. The extract solution was washed with an aqueous saline solution, dried over anhydrous magnesium sulfate, and then concentrated under reduced pressure. The concentrate was purified by means of a column chromatography (silica gel 120 g; dichloromethane-methanol 20:1) to give 780 mg of 2-[[1,5-bis(diphenylmethoxy)-4-pyridon-2-yl]methylthio]-5-mercapto-1,3,4-thiadiazole. IR(KBr): 3034, 1609, 1558, 1527, 1492, 1450 cm$^{-1}$. $^1$H-NMR(DMSO-d$_6$) ε: 3.88(2H,s), 6.03(1H,s), 6.32(1H,s), 6.42(1H,s), 7.10-7.70(20H,m), 7.79(1H,s)

REFERENCE EXAMPLE 4

In place of 2-chloromethyl-1,5-bis(diphenylmethoxy)-4-pyridone in Reference Example 3, 2-chloromethyl-1-methoxy-5-(4-methoxybenzyloxy)-4-pyridone was employed. Substantially the same reaction as Reference Example 3 was conducted to give 2-[[1-methoxy- 5-(4-methoxybenzyloxy)-4-pyridon-2-yl]methylthio]-5-mercapto-1,3,4-thiadiazole. $^1$H-NMR(DMSO-d$_6$) ε: 3.76(3H,s), 4.06(3H,s), 4.39(2H,s), 4.91(2H,s), 6.28(1H,s), 6.94(2H,d,J=8 Hz), 7.35(2H,d,J=8 Hz), 8.05(1H,s)

REFERENCE EXAMPLE 5

Substantially the same reaction as Reference Example 3 was conducted, excepting the use of 4-cyano-3,5-dimercaptoisothiazole disodium salt in place of 2,5-dimercapto-1,3,4-thiadiazole, to give 4-cyano-3-[[1,5-bis(diphenylmethoxy)-4-pyridon-2-yl]methylthio-5-mercaptoisothiazole. IR(KBr): 2200, 1608, 1556, 1321 cm$^{-1}$. $^1$H-NMR(DMSO-d$_6$) ε: 3.97(2H,s), 6.02(1H,s), 6.32(1H,s), 6.39(1H,s), 7.1-7.65(20H,m), 7.73(1H,s)

REFERENCE EXAMPLE 6

2-Hydroxymethyl-5-(4-methoxybenzyloxy)-4-pyrone (2.62 g) was dissolved in dichloromethane (48 ml). To the solution was added, while stirring at room temperature, p-toluenesulfonic acid (100 mg). To the mixture was added dropwise 3,4-dihydro-2H-pyrane (2.28 ml). The mixture was stirred for 3 hours at room temperature. The reaction mixture was washed with an aqueous solution of sodium hydrogencarbonate and an aqueous saline solution, which was dried over anhydrous magnesium sulfate, followed by concentration under reduced pressure. The concentrate was crystallized from ether, and the crystals were collected by filtration to give 1.85 g of 5-(4-methoxybenzyloxy)-2-(tetrahydropyran-2-yl)oxymethyl-4-pyrone as colorless crystals, m.p.95°-96° C. IR(KBr): 3070, 2940, 1650, 1620, 1510, 1450, 1210, 1020 cm$^{-1}$. $^1$H-NMR(DMSO-d$_6$) ε: 1.4-1.8(6H,m), 3.4-3.55(1H,m), 3.65-3.85(4H,m), 4.40(2H,ABq,J=14 Hz), 4.07(1H,br.), 4.86(2H,s), 6.38(1H,s), 6.93(2H,d,J=8 Hz), 7.33(2H,d,J=8 Hz), 8.16(1H,s)

REFERENCE EXAMPLE 7

The compound obtained in Reference Example 6 (1.73 g) was dissolved in methanol (50 ml), to which were added, while stirring at room temperature, 1-(2-aminoethyl)-5-mercapto-1H-tetrazole hydrochloride (3.62 g) and 2N sodium hydroxide (20 ml). The mixture was stirred for 5 days at room temperature and for further 5 days at 40° C., which was then washed with ethyl acetate. The reaction mixture was adjusted to pH 2 with 3N HCl, which was subjected to extraction with ethyl acetate and THF (3:1). The extract solution was washed with an aqueous saline solution, then dried over anhydrous magnesium sulfate. The solvent was distilled off under reduced pressure. The residue was purified by means of a column chromatography (silica gel 100 g; dichloromethane-ethanol) to give 1.38 g of 5-mercapto-1-[2-[5-(4-methoxybenzyloxy)-2-(tetrahydropyran-2-yl)oxymethyl-4-pyridon-1-yl]ethyl-1H-tetrazole as pale yellow crystals, m.p.116°-117° C. IR(KBr): 2940, 1630, 1570, 1510, 1240, 1030 cm$^{-1}$. $^1$H-NMR(DMSO-d$_6$) ε: 1.4-1.8(6H,m), 3.65-3.8(1H,m), 3.76(3H,s), 4.25-4.60(4H,m), 4.7-4.8(3H,m), 6.21(1H,s), 6.93(2H,d,J=8 Hz), 7.35(2H,d,J=8 Hz), 7.36(1H,s)

REFERENCE EXAMPLE 8

Substantially the same reaction as in Reference Example 1 and 2 was conducted, excepting the use of 1-methoxy-5-(4-methoxybenzyloxy)-2-phthalimidomethyl-4-pyridone in place of 1,5-bis(diphenylmethoxy)-2-phthalimidomethyl-4-pyridone, to give 5-mercapto-1-[[1-methoxy-5-(4-methoxybenzyloxy)-4-pyridon-2-yl]methyl]-1H-tetrazole, m.p.172°-175° C. IR(KBr): 1605, 1550, 1510 cm$^{-1}$. $^1$H-NMR(DMSO-d$_6$) ε: 3.77(3H,s), 4.11(3H,s), 4.95(2H,s), 5.53(2H,s), 5.94(1H,s), 6.96(2H,d,J=8.4 Hz), 7.37(2H,d,J=8.4 Hz), 8.17(1H,s)

REFERENCE EXAMPLE 9

Substantially the same reaction as in Reference Example 3 was conducted, excepting the use of 2,4-thiazolidindithione in place of 2,5-dimercapto-1,3,4-thiadiazole, to give 2-[[1,5-bis(diphenylmethoxy)-4-pyridon-2-yl]methylthio]-4-mercaptothiazole. IR(KBr): 3332, 3244, 1608, 1560 cm$^{-1}$. $^1$H-NMR(DMSO-d$_6$) ε:

3.62(2H,brs), 5.84(1H,s), 6.26(1H,s), 6.43(1H,s), 7.05–7.50(20H,m), 7.73(1H,s)

REFERENCE EXAMPLE 10

Substantially the same reaction as in Reference Example 3, excepting the use of 3,5-dimercapto-4-methyl-1,2,4-triazole in place of 2,5-dimercapto-1,3,4-thiadiazole, to give 3-[[1,5-bis(diphenylmethoxy)-4-pyridon-2-yl]methylthio]-5-mercapto-4-methyl-1,2,4-triazole. IR(KBr): 1610, 1562, 1520 cm$^{-1}$. $^1$H-NMR(CDCl$_3$) ε: 3.44(3H,s), 3.78(2H,s), 5.93(1H,s), 6.13(1H,s), 6.63(1H,s), 6.89(1H,s), 7.15–7.45(20H,m)

REFERENCE EXAMPLE 11

In DMF (100 ml) was suspended 1-hydroxy-2-hydroxymethyl-5-(4-methoxybenzyloxy)-4-pyridone (7.0 g). To the suspension were added anhydrous potassium carbonate (4.19 g) and 2-(tetrahydropyran-2yl)oxyethylbromide (6.33 g). The mixture was stirred for 20 hours at room temperature. The reaction mixture was concentrated under reduced pressure, to which were added dichloromethane and a saturated aqueous saline solution. The mixture was shaken, then the organic layer was separated and dried over anhydrous magnesium sulfate. The solvent was distilled off under reduced pressure, and the residue was purified by means of a silica gel column chromatography (silica gel 150 g, ethyl acetate-ethanol=3:1) to give a foamy product (8.71 g). The foamy product thus obtained (7.48 g) was dissolved in dichloromethane (200 ml), to which was added carbon tetrachloride (35.6 ml). To the mixture was then added, at $-70°$ C., hexamethylphosphorus triamide(4.35 ml). The reaction mixture was warmed up to room temperature, stirred for 15 hours, then washed with water and a saturated aqueous saline solution, successively, followed by drying over anhydrous magnesium sulfate. The solvent was distilled off under reduced pressure to give 9.09 g of 6-chloromethyl-3-(4-methoxybenzyloxy)-1-[2-(tetrahydropyran-2-yl)oxyethoxy]-4-pyridone as an oily product. The oily product thus obtained was dissolved in DMF (75 ml), to which was added potassium phthalimide (3.75 g). The mixture was stirred for 15 hours at room temperature. The solvent was distilled off under reduced pressure. To the residue were added ethyl acetate and water. The mixture was shaken, then the organic layer was separated, followed by drying over anhydrous magnesium sulfate. The resultant organic layer was concentrated to dryness under reduced pressure to give 7.90 g of 3-(4-methoxybenzyloxy)-6-phthalimidomethyl-1-[2-(tetrahydropyran-2-yl)oxyethoxy]-4-pyridone as a foamy product. $^1$H-NMR(CDCl$_3$) ε: 1.4–1.9(6H,m), 3.45–3.95(2H,m), 3.81(3H,s), 4.00 and 4.07(2H,each t,J=4 Hz), 4.42(2H,t,J=4 Hz), 4.6–4.7(1H,m), 4.92(2H,s), 5.07(2H,s), 6.13(1H,s) 6.88(2H,d,J=9 Hz), 7.32(2H,d,J=9 Hz), 7.34(1H,s), 7.75–7.95(4H,m)

REFERENCE EXAMPLE 12

Substantially the same reaction as in Reference Example 1 and 2 was conducted, excepting the use of the compound obtained in Reference Example 11 in place of 1,5-bis(diphenylmethoxy)-2-phthalimidomethyl-4-pyridone, to give 5-mercapto-1-[[5-(4-methoxybenzyloxy)- 1-[2-(tetrahydropyran-2-yl)oxyethoxy]-4-pyridon-2-yl]methyl]-1H-tetrazole, m.p.145°–147° C. IR(KBr): 2940, 1615, 1560, 1520 cm$^{-1}$. $^1$H-NMR(DMSO-d$_6$) ε: 1.3–1.8(6H,m), 3.2–3.5(2H,m), 3.76(3H,s), 3.8–4.0(2H,m), 4.5–4.6(2H,m), 4.6–4.7(1H,m), 4.94(2H,s), 5.57(2H,s), 5.80(1H,s), 6.95(2H,d,j=8 Hz), 7.35(2H,d,J=8 Hz), 8.07(1H,s)

REFERENCE EXAMPLE 13

1-(2-Aminoethyl)-5-mercapto-1H-tetrazole hydrochloride (2.72 g) was dissolved in a 2N aqueous solution of sodium hydroxide (15 ml). To the solution was added a solution of 3-(4-methoxybenzyloxy)-2-methyl-4-pyrone (1.85 g) in ethanol (38 ml). The mixture was heated for 4 days under reflux, which was then concentrated under reduced pressure. To the concentrate were added water and ethyl acetate. The mixture was shaken. The aqueous layer was taken, whose pH was adjusted to 1–2 with 2N HCl under ice-cooling to thereby cause precipitation of crystals. To the reaction mixture were added ethyl acetate and THF, which was then stirred, followed by collecting crystals by filtration. Washing the crystals with dilute hydrochloric acid and water, successively afforded 5-mercapto-1-[2-[3-(4-methoxybenzyloxy)-2-methyl-4-pyridon-1-yl]ethyl]-1H-tetrazole (976 mg). IR(KBr): 3425, 3000, 2960, 2930, 2830, 1620, 1585, 1540, 1515 cm$^{-1}$. $^1$H-NMR(DMSO-d$_6$) ε: 2.20(3H,s), 3.76(3H,s), 4.42–4.58(4H,m), 4.92(2H,s), 6.30(1H,d,J=7 Hz), 6.91 (2H,d,J=9 Hz), 7.32(2H,d,J=9 Hz), 7.49 (1H,d,J=7 Hz)

REFERENCE EXAMPLE 14

Substantially the same reaction as in Reference Example 13 was conducted, excepting the use of 3-(2-aminoethyl)-5-mercapto-1,2,4-thiadiazole hydrobromide in place of 1-(2-aminoethyl)-5-mercapto-1H-tetrazole hydrochloride, to give 5-mercapto-3-[[3-(4-methoxybenzyloxy)-2-methyl-4-pyridon-1-yl]ethyl]-1,2,4-thiadiazole. IR(KBr): 3425, 2930, 2830, 2720, 2625, 1610, 1560, 1510 cm$^{-1}$. $^1$H-NMR(DMSO-d$_6$) ε: 2.33(3H,s), 3.13(2H,t,J=7 Hz), 3.76(3H,s), 4.49(2H,t,J=7 Hz), 4.99(2H,s), 6.73(1H,d,J=7 Hz), 6.93(2H,d,J=9 Hz), 7.35(2H,d,J=9 Hz), 7.97(1H,d,J=7 Hz)

REFERENCE EXAMPLE 15

Sodium hydroxide (4.0 g) and ethanol (200 ml) were added to a mixture of 3-(4-methoxybenzyloxy)-2-methyl-4-pyrone (9.85 g), glycine (3.0 g) and water (440 ml), followed by stirring for 7 days at room temperature. The reaction mixture was adjusted to pH 2 with conc. hydrochloric acid, which was concentrated under reduced to pressure to a volume of about 200 ml. Resulting crystalline precipitates were collected by filtration and washed with water to give 2-[3-(4-methoxybenzyloxy)-2-methyl-4-pyridon-1-yl]acetic acid (7.22 g). IR(KBr): 3047, 1691, 1635, 1250 cm$^{-1}$. $^1$H-NMR(DMSO-d$_6$) ε: 2.04(3H,s), 3.75(3H,s), 4.78(2H,s), 4.96(2H,s), 6.16(1H,d,J=8 Hz), 6.95–7.0(2H,m), 7.25–7.4(2H,m), 7.57(1H,d,J=8 Hz)

REFERENCE EXAMPLE 16

The compound obtained in Reference Example 15 (909 mg) was dissolved in DMF (20 ml). To the solution were added, at room temperature, 1-hydroxybenzotriazole (408 mg) and dicyclohexylcarbodiimide (636 mg). The mixture was stirred for 30 minutes. To this reaction mixture was added a solution of 2-amino-5-mercapto-1,3,4-thiadiazole (402 mg) in DMF (4 ml), followed by stirring overnight at room temperature. Insolubles were filtered off. To the filtrate was added water. Resulting crystalline precipitates were collected by filtration, followed by washing with water and ethyl acetate, successively to give 2-mercapto-5-[2-[3-(4-methoxybenzyloxy-2-methyl-4-pyridon-1-yl]acetamido]-1,3,4-thiadiazole (890 mg). IR(KBr): 3462, 1709, 1624, 1416, 1383 cm$^{-1}$. $^1$H-NMR(DMSO-d$_6$) ε: 2.01(3H,s), 3.75(3H,s), 4.86(2H,s), 4.95(2H,s), 6.15(1H,d,J=8 Hz), 6.85–6.95(2H,m), 7.25–7.40(2H,m), 7.55(2H,d,J=8 Hz)

REFERENCE EXAMPLE 17

Substantially the same reaction as in Reference Example 16 was conducted, excepting the use of 1-amino-5-mercapto-1H-tetrazole in place of 2-amino-5-mercapto-1,3,4-thiadiazole, to give 5-mercapto-1-[2-[3-(4-methoxybenzyloxy)-2-methyl-4-pyridon-1-yl]acetamido]-1H-tetrazole. IR(KBr): 3427, 1716, 1626, 1554, 1512 cm$^{-1}$. $^1$H-NMR(DMSO-d$_6$) ε: 2.25(3H,s), 3.75(3H,s), 4.88(2H,s), 4.93(2H,s), 6.14(1H,d,J=7 Hz), 6.91(2H,d,J=9 Hz), 7.35(2H,d,J=9 Hz), 7.61(1H,d,J=7 Hz)

EXAMPLE 1

Sodium 7β-[2-(5-amino-1,2,4-thiadiazol-3-yl)-(Z)-2-methoxyiminoacetamido]-3-[[1-[(1,5-dihydroxy-4-pyridon-2-yl)methyl]-1H-tetrazol-5-yl]thiomethyl]-3-cephem-4-carboxylate

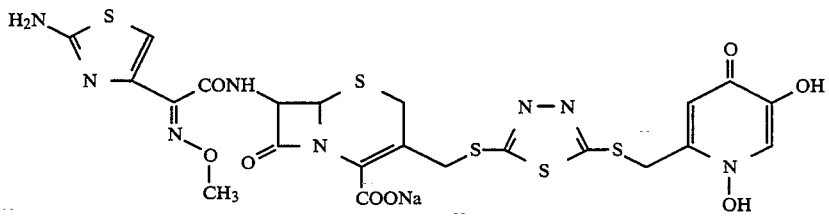

In DMF (2 ml) was suspended 1-[(1-diphenylmethaxy-5-hydroxy-4-pyridon-2-yl)methyl]-5-mercapto-1H-tetrazole (91 mg). To the suspension was added triethylamine (0.05 ml) to make a solution. To this solution was added, under ice-cooling, a solution of sodium 7β-[2-(5-amino-1,2,4-thiadiazol-3-yl)-(Z)-2-methoxyiminoacetamido]-3-hydroxymethyl-3-cephem-4-carboxylate (146 mg) in DMF (3 ml). To the mixture was then added ethyl o-phenylene phosphate (132 mg), and the mixture was stirred for 2 hours. The solvent was distilled off under reduced pressure. To the residue were added, under ice-cooling, trifluoroacetic acid (2 ml) and anisole (0.5 ml), followed by stirring for 1.5 hour. To the reaction mixture was added ethyl ether (4 ml). Resulting solid matter was collected by filtration, which was dissolved in acetonitrile-water (1:1). The solution was adjusted to pH 7, which was then concentrated under reduced pressure. The concentrate was purified by means of a SP-207 column chromatography (SP-207 70 ml; acetonitrile-water 8:92), followed by lyophilization to give the title compound. IR(KBr): 1765, 1620 cm$^{-1}$. $^1$H-NMR(DMSO-d$_6$) ε: 3.92(3H,s), 4.25(2H,ABq,J=13 Hz), 4.85(1H,d,J=5 Hz), 5.54(2H,s), 5.60(1H,dd,J=5&9 Hz), 6.04(1H,s), 7.58(1H,s)

EXAMPLE 2

Sodium 7β-[2-(2-aminothiazol-4-yl)-(Z)-2-methoxyiminoacetamido]-3-[[5-[(1,5-dihydroxy-4-pyridon-2-yl)methylthio]-1,3,4-thiadiazol-2-yl]thiomethyl]-3-cephem-4-carboxylate

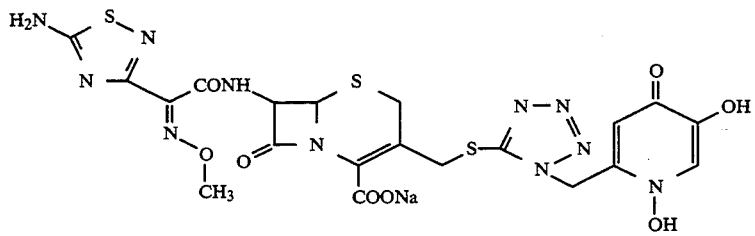

In DMF (5 ml) were dissolved sodium 7β-[2-(2-aminothiazol-4-yl)-(Z)-2-methoxyiminoacetamido]-3-hydroxymethyl-3-cephem-4-carboxylate (363 mg) and 2-[[1,5-bis(diphenylmethoxy)-4-pyridon-2-yl]methyl]-5-mercapto-1,3,4-thiadiazole (746 mg). To the solution was added, while stirring at 0° C., ethyl o-phenylene phosphate (1.2 g). The reaction mixture was stirred for one hour, which was then subjected to a silica gel column chromatography (silica gel 120 g), eluting with a mixture of acetonitrile and water (1:0→7:1). The eluate was concentrated under reduced pressure, followed by lyophilization. The resulting powdery product was suspended in dichloromethane (5 ml). To the suspension were added, at 0° C., anisole (1 ml) and trifluoroacetic acid (6 ml), successively, then the mixture was stirred for 2 hours. The reaction mixture was concentrated, to which was added isopropylether. Resulting precipitates were collected by filtration, to which was added water (100 ml), followed by adjusting the pH to 7 with a 1N aqueous solution of sodium hydroxide. This aqueous solution was washed with ether, followed by concentration to a volume of about 50 ml. The concentrate was purified by means of a XAD-2 column chromatography (XAD-2 150 ml; ethanol-water 0→10%), followed by lyophilization. The resulting powdery product was purified again by means of a LH-20 column chromatography (LH-20 600 ml; water) to afford 91 mg of the title compound. IR(KBr): 3425, 1765, 1659, 1610, 1529, 1400, 1358, 1178, 1041 cm$^{-1}$. $^1$H-NMR(D$_2$O) ε: 3.62(2H,ABq,J=17.8 Hz), 4.00(3H,s), 4.28(2H,ABq,J=13.4 Hz), 4.40(2H,s), 5.19(1H,d,J=4.6 Hz), 5.79(1H,d,J=4.6 Hz), 6.56(1H,brs), 7.04(1H,s), 7.60(1H,brs)

EXAMPLE 3

Sodium 7β-[2-(5-amino-1,2,4-thiadiazol-3-yl)-(Z)-2-methoxyiminoacetamido]-3-[[4-cyano-3-[(1,5-dihydroxy-4-pyridon-2-yl)methylthio]isothiazol-5-yl]thiomethyl]-3-cephem-4-carboxylate

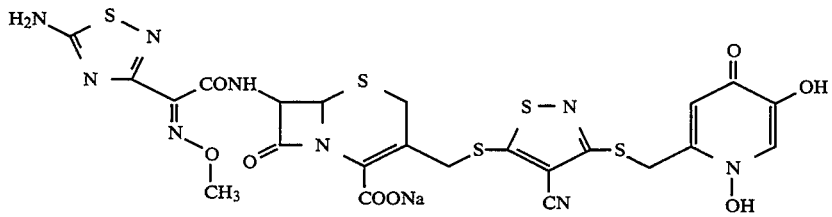

In DMF (4 ml) were dissolved sodium 7β-[2-(5-amino-1,2,4-thiadiazol-3-yl)-(Z)-2-methoxyiminoacetamido]-3-hydroxymethyl-3-cephem-4-carboxylate (1.2 g) and 4-cyano-3-[[1,5-bis(diphenylmethoxy)-4-pyridon-2-yl]methylthio]-5-mercaptoisothiazole (671 mg). To the solution was added, while stirring at 0° C. ethyl o-phenylene phosphate (0.8 g). The reaction mixture was stirred for 2.5 hours at 0° C., which was subjected to a silica gel column chromatography (silica gel 100 g), eluting with a mixture of acetonitrile and water (1:0→20:1). The eluate was concentrated under reduced pressure and then lyophilized. The resulting powdery product was suspended in dichloromethane (10 ml). To the suspension were added at 0° C. anisole (1 ml) and trifluoroacetic acid (5 ml), successively. The mixture was stirred for 1.5 hour. The reaction mixture was concentrated under reduced pressure. The concentrate was diluted with water (100 ml), whose pH was adjusted to 7 with a 1N aqueous solution of sodium hydroxide. This aqueous solution was washed with ethyl acetate, which was then concentrated under reduced pressure to a volume of about 50 ml. The concentrate was purified by means of a HP-20 column chromatography (HP-20 150 ml; ethanol-water 0→20%), followed by lyophilization to afford 80 mg of the title compound. IR(KBr): 2200, 1763, 1616, 1520, 1480, 1041 cm$^{-1}$. $^1$H-NMR(D$_2$O) ε: 3.63(2H,ABq,J=18 Hz), 4.08(3H,s), 4.26(2H,ABq,J=13 Hz), 4.47(2H,s), 5.21(1H,d,J=4.6 Hz), 5.83(1H,d,J=4.6 Hz), 6.88(1H,s), 7.81(1H,s)

EXAMPLE 4

Sodium 7β-[2-(5-amino-1,2,4-thiadiazol-3-yl)-(Z)-2-methoxyiminoacetamido]-3-[[5-[(1,5-dihydroxy-4-pyridon-2-yl)methylthio]-1,3,4-thiadiazol-2-yl]thiomethyl]-3-cephem-4-carboxylate

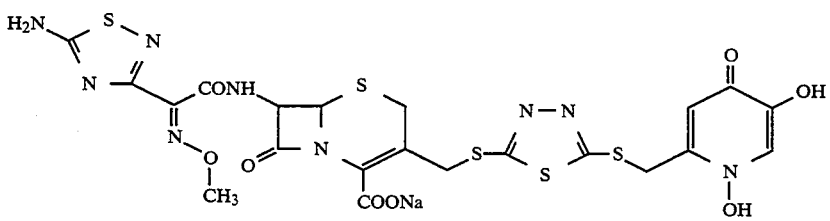

Substantially the same reaction as in Example 2 was conducted, excepting the use of sodium 7β-[2-(5-amino-1,2,4-thiadiazol-3-yl)-(Z)-2-methoxyiminoacetamido]-3-hydroxymethyl-3-cephem-4-carboxylate in place of sodium 7β-[2-(2-aminothiazol-4-yl)-(Z)-2-methoxyiminoacetamido]-3-hydroxymethyl-3-cephem-4-carboxylate, to give the title compound. IR(KBr): 3385, 3219, 1762, 1672, 1616, 1572, 1406, 1043 cm$^{-1}$. $^1$H-NMR(DMSO-d6)) ε: 3.92(3H,s), 4.2–4.4(3H,m), 4.65–4.8(1H,m), 5.0–5.1(1H,m), 5.67(1H,d,J=5 Hz), 7.68(1H,brs)

EXAMPLE 5

Sodium 7β- [2-(2-aminothiazol-4-yl)-(Z)-2-methoxyiminoacetamido]-3-[[5-[(5-hydroxy-1-methoxy-4-pyridon-4-pyridon-2-yl)methylthio]-1,3,4-thiadiazol-2-yl]thiomethyl]-3-cephem-4-carboxylate

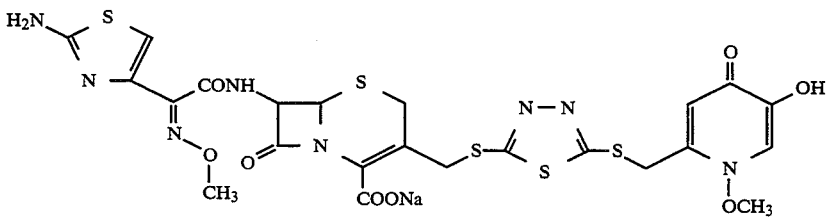

Substantially the same reaction as in Example 2 was conducted, excepting the use of 2-[[1-methoxy-5-(4-methoxybenzyloxy)-4-pyridon-2-yl]methylthio]mercapto-1,3,4-thiadiazole in place of 2-[[1,5-bis(diphenylmethoxy)-4-pyridon-2-yl]methylthio]-5-mercapto-1,3,4-thiadiazole, to afford the title compound. IR(KBr): 3423, 3207, 1770, 1674, 1612, 1600, 1537, 1041 cm$^{-1}$. $^1$H-NMR(DMSO-d6) ε: 3.84(3H,s), 4.07(3H,s), 4.41(2H,ABq,J=11.8 Hz), 4.50(2H,s), 5.10(1H,brd,J=5.0 Hz), 6.25(1H,brs), 7.22(2H,brs), 7.95(1H,brs), 8.58(1H,d,J=9 Hz)

EXAMPLE 6

Sodium 7β-[2-(5-amino-1,2,4-thiadiazol-3-yl)-(Z)-2-methoxyiminoacetamido]-3-[[5-[(5-hydroxy-1-methoxy-4-pyridon-2-yl)methylthio]-1,3,4-thiadiazol-2-yl]thiomethyl]-3-cephem-4-carboxylate

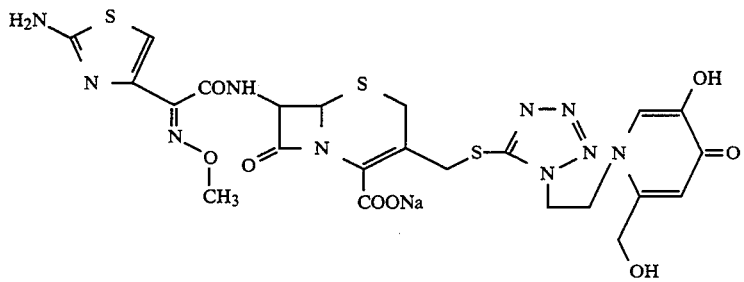

IR(KBr): 3427, 1765, 1668, 1591, 1531, 1389, 1356, 1038 cm$^{-1}$. $^1$H-NMR(D$_2$O) ε: 3.54(2H,ABq,J=17.4 Hz), 4.01(3H,s), 4.14(2H,ABq,J=13.2 Hz), 4.49(2H,s), 4.5–4.7(2H,m), 5.20(1H,d,J=4.6 Hz), 5.78(1H,d,J=4.6 Hz), 6.60(1H,s), 7.04(1H,s), 7.20(1H,s)

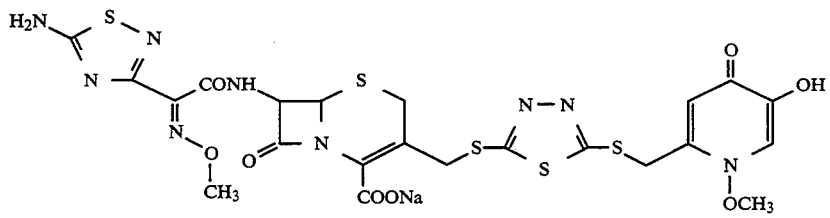

Substantially the same reaction as in Example 3 was conducted, excepting the use of 2-[[1-methoxy-5-(4-methoxybenzyloxy)-4-pyridon-2-yl]methylthio]-5-mercapto-1,3,4-thiadiazole in place of 4-cyano-3-[[1,5-bis(-diphenylmethoxy)-4-pyridon-2-yl]methylthio]-5-mercaptoisothiazole, to afford the title compound. IR(KBr): 3407, 3194, 1765, 1602, 1574, 1527, 1403, 1385, 1360 cm$^{-1}$. $^1$H-NMR(DMSO-d$_6$) ε: 3.91(3H,s), 4.06(3H,s), 4.36(2H,ABq,J=13 Hz), 4.51(2H,s), 5.03(1H,d,J=4.8 Hz), 5.63(1H,dd,J=4.8&8.6 Hz), 6.24(1H,s), 7.93(1H,s), 8.14(2H,brs), 9.50(1H,d,J=8.6 Hz)

Likewise, compounds of the following Examples 7 to 16 were obtained.

EXAMPLE 7

Sodium 7β-[2-(2-aminothiazol-4-yl)-(Z)-2-methoxyiminoacetamido]-3-[[1-[2-(3-hydroxy-6-hydroxymethyl-4-pyridon-1-yl)ethyl]-1H-tetrazol-5-yl]thiomethyl]-3-cephem-4-carboxylate

EXAMPLE 8

Sodium 7β-[2-(5-amino-1,2,4-thiadiazol-3-yl)-(Z)-2-methoxyiminoacetamido]-3-[[1-[2-(3-hydroxy-6-hydroxymethyl-4-pyridon-1-yl)ethyl]-1H-tetrazol-5-yl]thiomethyl]-3-cephem-4-carboxylate

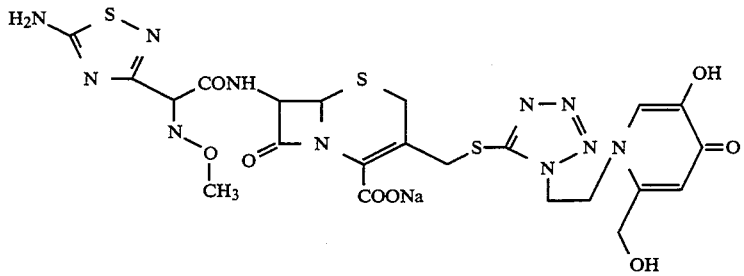

IR(KBr): 3384, 1765, 1662, 1568, 1410, 1041 cm$^{-1}$. $^1$H-NMR(D$_2$O) ε: 3.53(2H,ABq,J=18 Hz), 4.10(3H,s), 4.13(2H,ABq,J=13.2 Hz), 4.49(2H,s), 4.5–4.65(2H,m), 4.85–5.0(2H,m), 5.19(1H,d,J=4.8 Hz), 5.82(1H,d,J=4.8 Hz), 6.60(1H,s), 7.21(1H,s)

EXAMPLE 9

Sodium 7β-[2-(2-aminothiazol-4-yl)-(Z)-2-methoxyiminoacetamido]-3-[[1-(1,5-dihydroxy-4-pyridon-2-yl)methyl-1H-tetrazol-5-yl]thiomethyl]-3-cephem-4-carboxylate

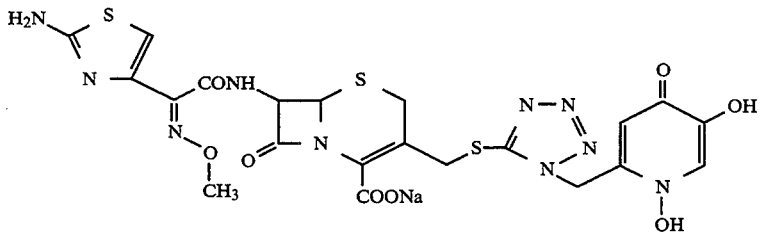

IR(KBr): 1765, 1660, 1610 cm⁻¹. ¹H-NMR(D₂O) ϵ: 3.57(2H,ABq,J=18 Hz), 4.05(3H,s), 4.24(2H,ABq,J=13 Hz), 5.16(1H,d,J=15 Hz), 5.77(1H,d,J=5 Hz), 5.58(2H,s), 6.83(1H,s), 7.02(1H,s), 7.71(1H,s)

EXAMPLE 10

Sodium 7β-[2-(5-amino-1,2,4-thiadiazol-3-yl)-(Z)-2-methoxyiminoacetamido]-3-[[1-[(5-hydroxy-1-methoxy-4-pyridon-2-yl)methyl]-1H-tetrazol-5-yl]thiomethyl]-3-cephem-4-carboxylate

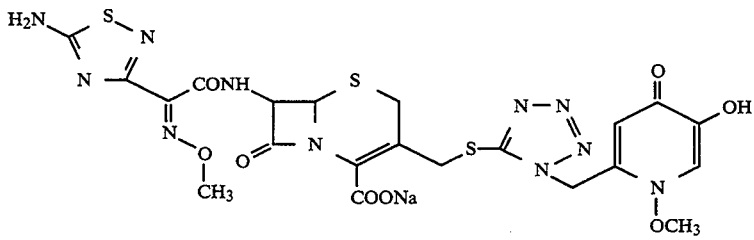

IR(KBr): 1760, 1600 cm⁻¹. ¹H-NMR(D₂O) ϵ: 3.56(2H,ABq,J=18 Hz), 4.06(3H,s), 4.07(3H,s), 4.27(2H,ABq,J=13 Hz), 5.15(1H,d,J=5 Hz) 5.80(1H,d,J=5 Hz), 5.71(2H,s), 6.51(1H,s), 7.98(1H,s)

EXAMPLE 11

Sodium 7β-[2-(2-aminothiazol-4-yl)-(Z)-2-methoxyiminoacetamido]-3-[[1-[(5-hydroxy-1-methoxy-4-pyridon-2-yl)methyl]-1H-tetrazol-5-yl]thiomethyl]-3-cephem-4-carboxylate IR(KBr): 1765, 1620 cm⁻¹. ¹H-NMR(D₂O) ϵ: 3.58(2H,ABq,J=18 Hz), 3.98(3H,s), 4.06(3H,s), 4.26(2H,ABq,J=13 Hz), 5.15(1H,d,J=5 Hz), 5.74(1H,d,J=5 Hz), 5.72(2H,s), 6.52(1H,s), 7.01(1H,s), 7.98(1H,s)

EXAMPLE 12

Sodium 7β-[2-(5-amino-1,2,4-thiadiazol-3-yl)-(Z)-2-ethoxyiminoacetamido]-3-[[1-[(5-hydroxy-1-methoxy-4-pyridon-2-yl)methyl]-1H-tetrazol-5-yl]thiomethyl]-3-cephem-4-carboxylate

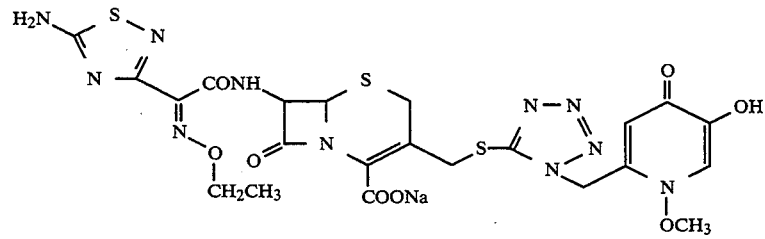

IR(KBr): 1765, 1620 cm⁻¹. ¹H-NMR(D₂O) ϵ: 1.32(3H,t,J=7 Hz), 3.57(2H,ABq,J=18 Hz), 4.06(3H,s), 4.27(2H,ABq,J=13 Hz), 4.35(2H,q,J=7 Hz), 5.16(1H,d,J=5 Hz), 5.80(1H,d,j=5 Hz), 5.71(2H,s), 6.52(1H,s), 7.98(1H,s)

EXAMPLE 13

Sodium 7β-[2-(5-amino-1,2,4-thiadiazol-3-yl)-(Z)-2-ethoxyiminoacetamido)-3-[[4-cyano-3-[(1,5-dihydroxy-4-pyridon-2-yl)methylthio]isothiazol-5-yl]thiomethyl]-3-cephem-4-carboxylate

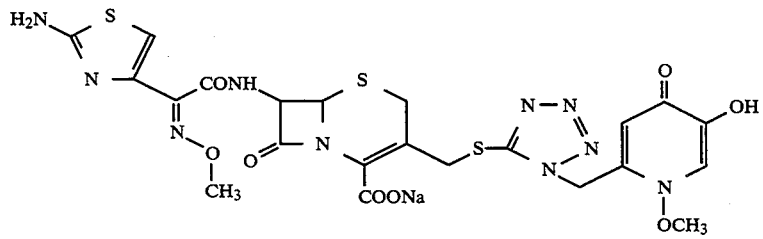

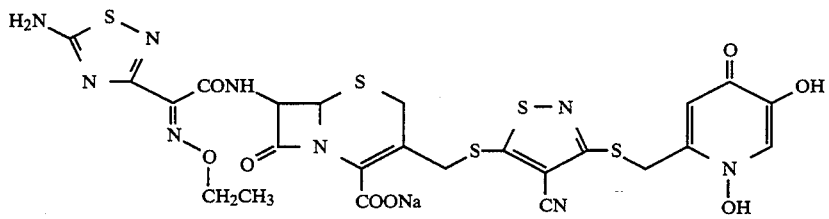

IR(KBr): 3417, 3200, 1765, 1614, 1529 cm⁻¹. ¹H-NMR(DMSO-d₆) ϵ: 1.26(3H,t,J=7 Hz), 4.1–4.25(3H,m), 4.43(2H,brs), 4.5–4.7(1H,m), 5.09(1h,d,J=4.4 Hz), 5.6–5.75(1H,m), 6.63(1H,brs), 7.66(1H,brs), 8.13(2H,brs), 9.45–9.60(1H,m)

EXAMPLE 14

Sodium 7β-[2-(5-amino-1,2,4-thiadiazol-3-yl)-(Z)-2-ethoxyiminoacetamido]-3-[[1-[(1,5-dihydroxy-4-pyridon-2-yl)methyl]-1H-tetrazol-5-yl]thiomethyl]-3-cephem-4-carboxyate

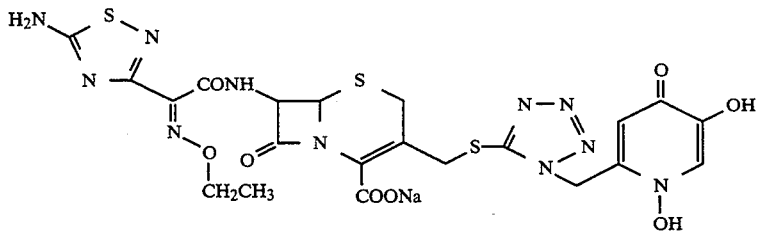

IR(KBr): 1770, 1670, 1620 cm⁻¹. ¹H-NMR(D₂O) ϵ: 1.32(3H,t,J=7 Hz), 3.43(1H,d,J=18 Hz), 3.72(1H,d,J=18 Hz), 4.09(1H,d,J=13 Hz), 4.37(1H,d,J=13 Hz), 4.35(2H,q,J=7 Hz), 5.15(1H,d,J=5 Hz), 5.66(2H,s), 5.80(1H,d,J=5 Hz), 7.09(1H,s), 7.91(1H,s)

EXAMPLE 15

Sodium 7β-[2-(5-amino-1,2,4-thiadiazol-3-yl)-(Z)-2-methoxymethoxyiminoacetamido]-3-[[1-[(5-hydroxy-1-methoxy-4-pyridon-2-yl)methyl]-1H-tetrazol-5-yl]thiomethyl]-3-cephem-4-carboxylate IR(KBr): 1770, 1665, 1610 cm⁻¹. ¹H-NMR(D₂O) ϵ: 3.43(3H, s), 3.42(1H,d,J=18 Hz), 3.71(1H, d,J=18 Hz), 4.07(3H,s), 4.14(1H,d,J=13 Hz), 4.39(1H, d,J=13 Hz), 5.18(1H,d,J=5 Hz), 5.66(2H,s), 5.72(2H, s), 5.83(1H,d,J=5 Hz), 6.52(1H,s), 8.00(1H, s)

EXAMPLE 16

Sodium 7β-[2-(5-amino-1,2,4-thiadiazol-3-yl)-(Z)-2-hydroxyiminoacetamido]-3-[[1-[(5-hydroxy-1-methoxy-4-pyridon-2-yl)methyl]-1H-tetrazol-5-yl]thiomethyl]-3-cephem-4-carboxylate

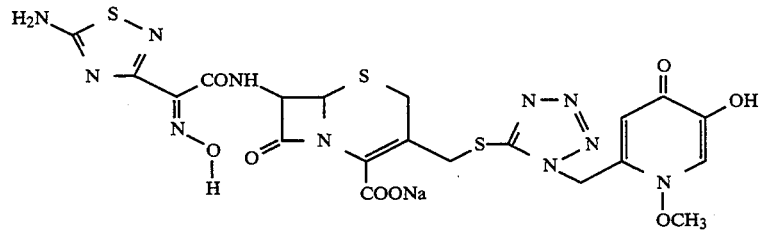

IR(KBr): 1765, 1670, 1610 cm⁻¹. ¹H-NMR (D₂O) ϵ: 3.39(1H,d,J=18 Hz), 3.70(1H,d,J=18 Hz), 4.07(3H,s), 4.16(1H,d,J=18 Hz), 4.37(1H,d,J=13 Hz), 5.17(1H,d,J=5 Hz), 5.72(2H,s), 5.84(1H,d,J=5 Hz), 6.52(1H,s), 8.00(1H,s)

EXAMPLE 17

Sodium 7β-[2-(5-amino-1,2,4-thiadiazol-3-yl)-(Z)-2-methoxyiminoacetamido]-3-[[4-[(1,5-dihydroxy-4-pyridon-2-yl)methylthio]thiazol-2-yl]thiomethyl]-3-cephem-4-carboxylate

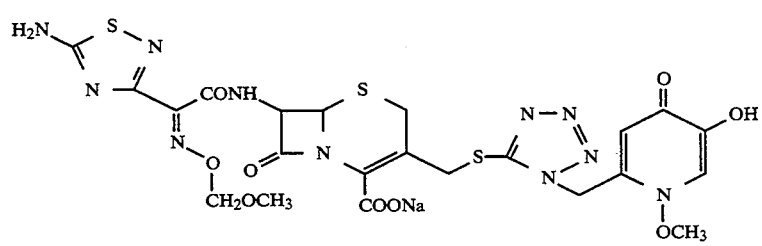

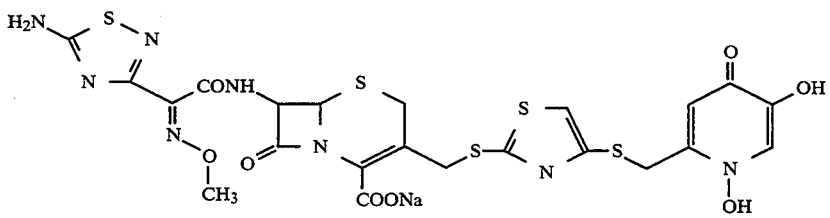

Substantially the same reaction as in Example 3 was conducted, excepting the use of 4-[[1,5-bis(diphenylmethoxy)-4-pyridon-2-yl]methylthio]-2-mercaptothiazole in place of 4-cyano-3-[[1,5-bis(diphenylmethoxy)-4-pyridon-2-yl]methylthio]-5-mercaptoisothiazole, to give the title compound. IR(KBr): 3188, 1765, 1666, 1616, 1529 cm$^{-1}$. $^1$H-NMR(D$_2$O) ϵ: 3.63(2H,ABq,J=18 Hz), 4.09(3H,s), 4.14(2H,s), 4.20(2H,ABq,J=14 Hz), 5.19(1H,d,J=5 Hz), 5.80(1H,d,J=5 Hz), 6.41(1H,s), 7.46(1H,s), 7.86(1H,s)

EXAMPLE 18

Sodium 7β-[2-(5-amino-1,2,4-thiadiazol-3-yl)-(Z)-2-methoxyiminoacetamido]-3-[[5-[1,5-dihydroxy-4-pyridon-2-yl)methylthio]-4-methyl-1,2,4-triazol-3yl]thiomethyl]-3-cephem-4-carboxylate

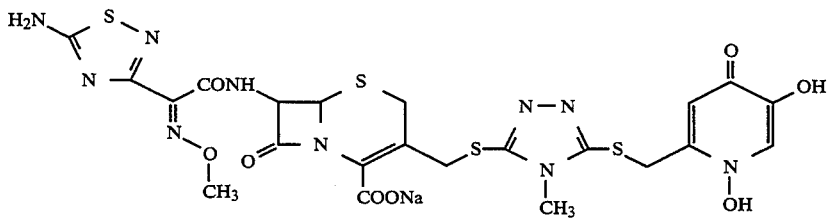

Substantially the same reaction as in Example 3 was conducted, excepting the use of 2-[[1,5-bis(diphenylmethoxy)-4-pyridon-2-yl]methylthio]-5-mercapto-4-methyl-1,2,4-triazole in place of 4-cyano-3-[[1,5-bis(diphenylmethoxy)-4-pyridon-2-yl]methylthio]-5-mercaptoisothiazole, to give the title compound. IR(KBr): 3317, 1763, 1672, 1618, 1531 cm$^{-1}$. $^1$H-NMR(D$_2$O) ϵ: 3.53(3H,s), 3.63(2H,ABq,J=18 Hz), 4.01(2H,ABq,J=13 Hz), 4.09(3H,s), 4.25(2H,s), 5.17(1H,d,J=5 Hz), 5.80(1H,d,J=5 Hz), 6.63(1H,s), 7.89(1H,s)

EXAMPLE 19

Sodium 7β-[2-(2-aminothiazol-4-yl)-(Z)-2-methoxyiminoacetamido]-3-[[1-[5-hydroxy-1-(2-hydroxyethyloxy)-4-pyridon-2-yl]methyl-1H-tetrazol-5-yl]thiomethyl]-3-cephem-4-carboxylate

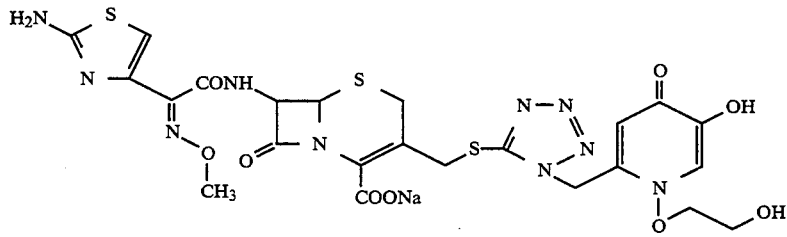

Substantially the same reaction as in Example 2 was conducted, excepting the use of 5-mercapto-1-[[5-(4-methoxybenzyl)-1-[2-(tetrahydropyran-2-yl)oxyethoxy]-4-pyridon-2-yl]methyl]-1H-tetrazole in place of 2-[(1,5-bis(diphenylmethoxy)-4-pyridon-2-yl]methylthio]-5-mercapto-1,3,4-thiadiazole, to give the title compound. IR(KBr): 1765, 1665, 1605, 1570, 1535 cm$^{-1}$. $^1$H-NMR(D$_2$O) ϵ: 3.42(1H,d,J=18 Hz), 3.71(1H,d,J=18 Hz), 3.89(2H,t,J=5 Hz), 3.99(3H,s), 4.15(1H,d,J=13 Hz), 4.37(1H,d,J=13 Hz), 4.43(2H,t,J=5 Hz), 5.16(1H,d,j=5 Hz), 5.76(1H,d,J=5 Hz), 5.77(2H,s), 6.43(1H,s), 7.01(1H,s), 8.00(1H,s)

EXAMPLE 20

Sodium 7β-[2-(5-amino-1,2,4-thiazol-3-yl)-(Z)-2-methoxyiminoacetamido]-3-[[1-[5-hydroxy-1-(2-hydroxyethyloxy)-4-pyridon-2-yl]methyl-1H-tetrazol-5-yl]thiomethyl]-3-cephem-4-carboxylate

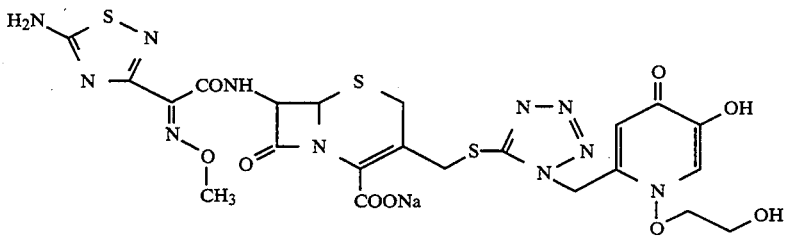

Substantially the same reaction as in Example 3 was conducted, excepting the use of 5-mercapto-1-[[5-(4-methoxybenzyl)-1-[2-(tetrahydropyran-2-yl)oxyethoxy]-4-pyridon-2-yl]methyl]-1H-tetrazole in place of 4-cyano-3-[[1,5-bis(diphenylmethoxy)-4-pyridon-2-yl]methylthio]-5-mercaptoisothiazole, to give the title compound. IR(KBr): 1765, 1670, 1600, 1570, 1530 cm$^{-1}$. $^1$H-NMR(DMSO-d$_6$) ε: 3.41(1H,d,J=18 Hz), 3.71(1H,d,J=18 Hz), 3.89(2H,t,J=5 Hz), 4.08(3H,s), 4.15(1H,d,J=13 Hz), 4.36(1H,d,J=13 Hz), 4.44(2H,t), 5.16(1H,d,J=5 Hz), 5.77(2H,s), 5.81(1H,d,J=5 Hz), 6.43(1H,s), 8.01(1H,s)

EXAMPLE 21

Sodium 7β-[2-(5-amino-1,2,4-thiadiazol-3-yl)-(Z)-2-methoxyiminoacetamido]-3-[[1-[2-(3-hydroxy-2-methyl-4-pyridon-1-yl)ethyl]-1H-tetrazol-5-yl]thiomethyl]-3-cephem-4-carboxylate Substantially the same reaction as in Example 3 was conducted, excepting the use of 5-mercapto-1-[2-[3-(4-methoxybenzyloxy)-2-methyl-4-pyridon-1-yl]ethyl]-1H-tetrazole in place of 4-cyano-3-[[1,5-bis(diphenylmethoxy)-4-pyridon-2-yl]-methylthio]5-mercaptoisothiazole, to give the title compound. IR(KBr): 3400, 2940, 1765, 1675, 1630, 1530, 1510 cm$^{-1}$. $^1$H-NMR(D$_2$O) ε: 2.36(3H,s), 3.50(2H,ABq,J=18 Hz), 4.10(3H,s), 4.11(2H,ABq,J=14 Hz), 5.19(1H,d,J=5 Hz), 5.82(1H,d,J=5 Hz), 6.34(1H,d,J=7 Hz), 7.13(1H,d,J=7 Hz)

EXAMPLE 22

Sodium 7β-[2-(5-amino-1,2,4-thiadiazol-3-yl)-(Z)-2-methoxyiminoacetamido]-3-[[3-[2-(3-hydroxy-2-methyl-4-pyridon-1-yl)ethyl]-1,2,4-thiadiazol-5-yl]thiomethyl]-3-cephem-4-carboxylate

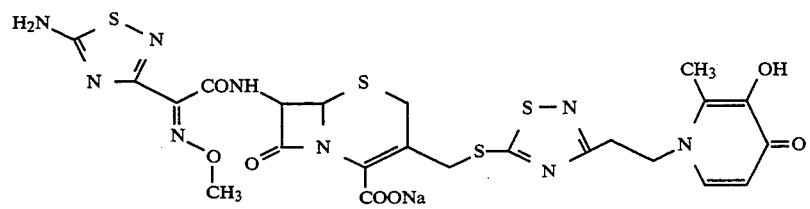

Substantially the same reaction as in Example 3 was conducted, excepting the use of 5-mercapto-3-[[3-(4-methoxybenzyloxy)-2-methyl-4-pyridon-1-yl]ethyl]-1,2,4-thiadiazole in place of 4-cyano-3-[[1,5-bis(diphenylmethoxy)-4-pyridon-2-yl]methylthio]-5-mercaptoisothiazole, to give the title compound. IR(KBr): 3300, 2940, 1770, 1680, 1630 cm$^{-1}$. $^1$H-NMR(D$_2$O) ε: 2.37(3H,s), 3.39(2H,t,J=7 Hz), 3.57(2H,ABq,J=18 Hz), 4.08(3H,s), 4.45–4.55(4H,m), 5.18(1H,d,J=5 Hz), 5.84(1H,d,J=5 Hz), 6.41(1H,d,J=7 Hz), 7.43(1H,d,J=7 Hz)

EXAMPLE 23

Sodium 7β-[2-(5-amino-1,2,4-thiadiazol-3-yl)-(Z)-2-ethoxyiminoacetamido]-3-[[1-[2-(3-hydroxy-2-methyl-4-pyridon-1-yl)ethyl]-1H-tetrazol-5-yl]thiomethyl]-3-cephem-4-carboxylate

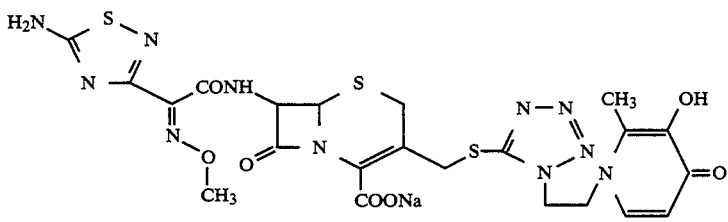

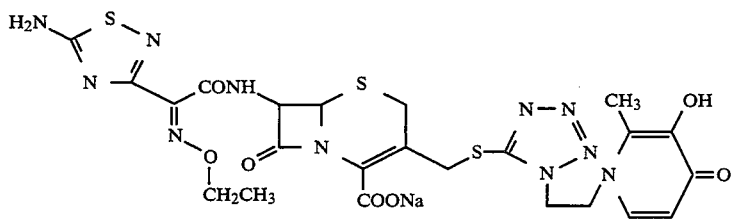

Substantially the same reaction as in Example 3 was conducted, excepting the use of sodium 7β-[2-(5-amino-1,2,4-thiadiazol-3-yl)-(Z)-2-ethoxyiminoacetamido]-3-hydroxymethyl-3-cephem-4-carboxylate in place of sodium 7β-[2-(5-amino-1,2,4-thiadiazol-3-yl)-(Z)-2-methoxyiminoacetamido]-3-hydroxymethyl-3-cephem-4-carboxylate, and of 5-mercapto-1-[2-[3-(4-methoxybenzyloxy)-2-methyl-4-pyridon-1-yl]ethyl]-1H-tetrazole in place of 4-cyano-3-[[1,5-bis(diphenylmethoxy)-4-pyridon-2-yl]methylthio]-5-mercaptoisothiazole, to give the title compound. IR(KBr): 3300, 2980, 1765, 1670, 1620, 1530, 1510 cm$^{-1}$. $^1$H-NMR(D$_2$O) ϵ: 1.36(3H,t,J=7 Hz), 2.36(3H,s), 3.51(2H,ABq,J=18 Hz), 4.11(2H,ABq,J=13 Hz), 4.38(2H,q,J=7 Hz), 5.19(1H,d,J=5 Hz), 5.82(1H,d,J=5 Hz), 6.34(1H,d,J=7 Hz), 7.13(1H,d,J=7 Hz)

EXAMPLE 24

Sodium 7β-[2-(5-amino-1,2,4-thiadiazol-3-yl)-(Z)-2-methoxyiminoacetamido]-3-[[5-[2-(3-hydroxy-2-methyl-4-pyridon-1-yl)acetamido]-1,3,4-thiadiazol-2-yl] thiomethyl]-3-cephem-4-carboxylate IR(KBr): 3406, 1763, 1624, 1549, 1510 cm$^{-1}$. $^1$H-NMR(D$_2$O) ϵ:2.35(3H,s), 3.65(2H,ABq,J=18 Hz), 4.08(3H,s), 4.13(2H, ABq,J=14 Hz), 5.15–5.25(3H,m) 5.78(1H,d,J=5 Hz), 6.57(1H,d,J=7 Hz), 7.67(1H,d,J=7 Hz)

EXAMPLE 25

Sodium 7β-[2-(5-amino-1,2,4-thiadiazol-3-yl)-(Z)-2-methoxyiminoacetamido]-3-[[1-[2-(3-hydroxy-2-methyl-4-pyridon1-yl)acetamido]-1H-tetrazol-5-yl]thiomethyl]-3-cephem-4-carboxylate

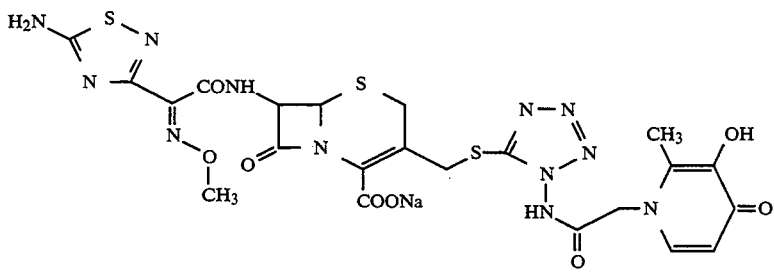

Substantially the same reaction as in Example 3 was conducted, excepting the use of 5-mercapto-1-[2-[3-(4-methoxybenzyloxy)-2-methyl-4-pyridon-1-yl]acetamido]-1H-tetrazole in place of 4-cyano-3-[[1,5-bis(diphenylmethoxy)-4-pyridon-2-yl]methylthio]-5-mercaptoisothiazole, to give the title compound. IR(KBr): 3460, 1763, 1676, 1632, 1595 cm$^{-1}$. $^1$H-NMR(D$_2$O) ϵ: 2.52(3H,s), 3.53(2H,ABq,J=17 Hz), 4.09(3H,s), 4.17(2H,ABq,J=14 Hz), 4.88(2H,s), 5.15(1H,d,J=4 Hz), 5.81(1H,d,J=4 Hz), 6.57(1H,d,J=7 Hz), 7.73(1H,d,J=7 Hz)

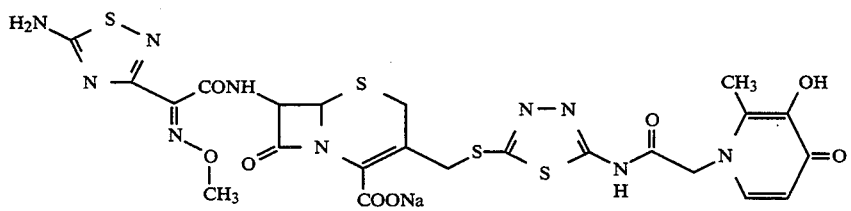

Substantially the same reaction as in Example 3 was conducted, excepting the use of 2-mercapto-5-[2-[3-(4-methoxybenzyloxy)-2-methyl-4-pyridon-1-yl]acetamido]-1,3,4-thiadiazole in place of 4-cyano-3-[[1,5-bis(diphenylmethoxy)-4-pyridon-2-yl]methylthio]-5-mercaptoisothiazole, to give the title compound.

EXAMPLE 26

Disodium 7β-[2-(5-amino-1,2,4-thiadiazol-3-yl)-(Z)-2-(1-carboxylato-1-methylethoxyimino)acetamido]-3-[[1-[(1,5-dihydroxy-4-pyridon-2-yl)methyl]-1H-tetrazol-5-yl]thiomethyl]-3-cephem-4-carboxylate

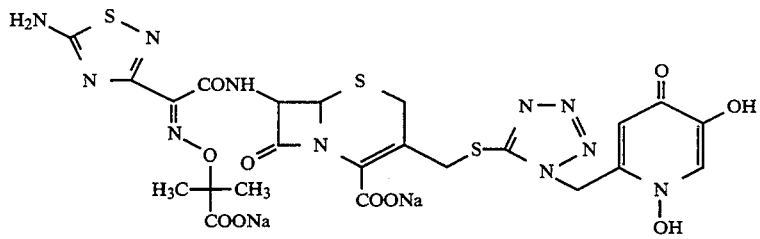

In DMF (6 ml) were dissolved sodium 7β-[2-(5-amino-1,2,4-thiadiazol-3-yl)-(Z)-2-[1-(4-methoxybenzyloxycarbonyl)-1-methylethoxyimino]acetamido]-3-hydroxymethyl-3-cephem-4-carboxylate (330 mg) and 1-[[1-diphenylmethoxy-5-(4-methoxybenzyloxy-4-pyridon-2-yl]methyl]-5-mercapto-1H-tetrazole (345 mg). To the solution was added, under ice-cooling, ethyl o-phenylene phosphate (550 mg), and the mixture was stirred for 1 hour. To the reaction mixture was added, under ice-cooling, iso-propyl ether (80 ml). The mixture was standed, then the resulting supernatant liquor was removed. The residue was subjected to a silica gel column chromatography (silica gel 40 g; acetonitrile-water 9:1). The eluate was concentrated under reduced pressure and then lyophilized. The resulting powdery product was suspended in dichloromethane (10 ml). To the suspension were added, under ice-cooling, anisole (1 ml) and trifluoroacetic acid (5 ml), successively. The mixture was stirred for 30 minutes. The reaction mixture was concentrated under reduced pressure. To the concentrate was added toluene (10 ml), which was then concentrated under reduced pressure again. The concentrate was dissolved in acetonitrile-water (1:1). The solution was adjusted to pH 7 with a 1N aqueous solution of sodium hydroxide, which was then concentrated under reduced pressure. The concentrate was washed with ethyl acetate, which was then concentrated under reduced pressure again. The concentrate was purified by means of an SP-207 column chromatography (SP-207, 70 ml; water-acetonitrile 88:12). The eluate was concentrated under reduced pressure, followed by lyophilization to give the title compound (84 mg). IR(KBr): 1760, 1620, 1530 cm$^{-}$ $^1$H-NMR(D$_2$O) ϵ: 1.53(6H,s), 3.34(1H,d,J=18 Hz), 3.67(1H,d,J=18 Hz), 4.10(1H,d,J=14 Hz), 4.34(1H,d,J=14 Hz), 5.13(1H,d,J=5 Hz), 5.65(2H,s), 5.81(1H,d,J=5 Hz), 7.06(1H,s), 7.89(1H,s)

Test Example 1 Minimal Inhibitory Concentrations (MIC)

The minimal inhibitory concentrations (MIC) of the test compounds were determined by the agar dilution method. More specifically, 0.25 ml each of aqueous solutions of the test compounds diluted by the serial dilution method was poured into petridishes. To each of these petridishes was poured 9.75 ml of Mueller-Hinton agar, followed by mixing. On each of these agar plates was a suspension of the test microorganism (about 10$^4$ CFU/spot). The lowest concentration of the test compounds inhibiting the growth of test microorganisms, after the incubation at 37° C. overnight, was taken as MIC.

TABLE 1

| Test Micro-organism | MIC (μg/ml) | | | |
|---|---|---|---|---|
| | Compd. of Ex. 3 | Compd. of Ex. 10 | Compd. of Ex. 12 | Compd. of Ex. 26 |
| P. aeruginosa | 0.1 | 0.2 | 0.2 | 0.025 |

TABLE 1-continued

| Test Micro-organism | MIC (μg/ml) | | | |
|---|---|---|---|---|
| | Compd. of Ex. 3 | Compd. of Ex. 10 | Compd. of Ex. 12 | Compd. of Ex. 26 |
| P9 P. aeruginosa NC-5 | 0.05 | 0.1 | 0.2 | 0.006 |

What is claimed is:

1. A compound of the formula

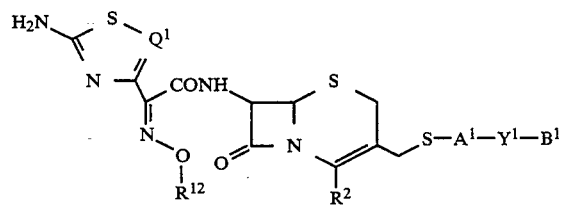

wherein Q$^1$ is N or CH;

R$^{12}$ is hydrogen, C$_{1-6}$ alkyl, C$_{1-4}$ alkoxy-C$_{1-6}$ alkyl or carboxy-C$_{1-6}$ alkyl;

R$^2$ is a carboxy group or an esterified carboxy group;

A$^1$ is a divalent group minus two hydrogen atoms selected from thiazole, isothiazole, thiadiazole, triazole or tetrazole Y$^1$ is —CH$_2$—, —CH$_2$CH$_2$—, —S—CH$_2$— —NH-CO—CH$_2$—; and B$^1$ is either

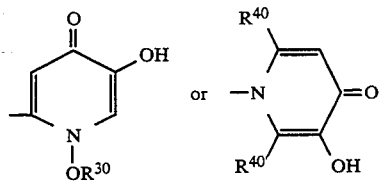

wherein each of R$^{30}$, R$^{40}$ and R$^{40'}$ is independently hydrogen, C$_{1-4}$ alkyl or hydroxy-C$_{1-4}$ alkyl or a pharmaceutically acceptable salt thereof.

2. A compound of claim 1 which is 7β-[2-(5-amino-1,2,4-thiadiazol-3-yl)-(Z)-2-(1-carboxy-1-methylethoxyimino)acetamido]-3-[[1-[(1,5-dihydroxy-4-pyridon-2-yl)methyl]-1H-tetrazol-5-yl]thiomethyl]-3-cephem-4-carboxylic acid or a pharmaceutically acceptable salt thereof.

3. The disodium salt of the compound of claim 2.

4. A compound as claimed in claim 1, wherein Q$^1$ stands for N; R$^{12}$ stands for a C$_{1-4}$ alkyl group optionally substituted with a carboxyl group; A$^1$ stands for a group of the formula:

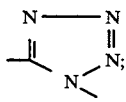

Y¹ stands for —CH$_2$—; and B¹ stands for a group of the formula:

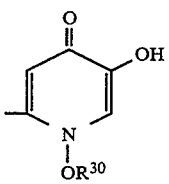

wherein R$^{30}$ stands for hydrogen atom or methyl.

5. An antimicrobial composition which comprises a pharmaceutically effective amount of a cephem compound or a pharmaceutically acceptable salt thereof as claimed in claim 1 and a pharmaceutically acceptable carrier, diluent or excipient.

6. A method for treating bacterial infection which comprises administering a pharmaceutically effective amount of a compound of the formula (I) according to claim 1 or a salt thereof optionally together with a pharmaceutically acceptable carrier, diluent or excipient to a patient suffering from bacterial infection.

* * * * *